*US006562319B2*

(12) United States Patent
Mishani et al.

(10) Patent No.: US 6,562,319 B2
(45) Date of Patent: May 13, 2003

(54) RADIOLABELED IRREVERSIBLE INHIBITORS OF EPIDERMAL GROWTH FACTOR RECEPTOR TYROSINE KINASE AND THEIR USE IN RADIOIMAGING AND RADIOTHERAPY

(75) Inventors: Eyal Mishani, Mevaseret Zion (IL); Iris Ben-David, Ashdod (IL); Yulia Rozen, Jerusalem (IL); Gluseppina Ortu, Jerusalem (IL); Alexander Levitzki, Jerusalem (IL)

(73) Assignees: Yissum Research Development Company of the Hebrew University of Jerusalem, Jerusalem (IL); Hadasit Medical Research Services and Development Ltd., Jerusalem (IL)

( * ) Notice: Subject to any disclaimer, the term of this patent is extended or adjusted under 35 U.S.C. 154(b) by 94 days.

(21) Appl. No.: 09/802,928

(22) Filed: Mar. 12, 2001

(65) Prior Publication Data

US 2002/0128553 A1 Sep. 12, 2002

(51) Int. Cl.[7] .................. A61K 51/00; A61M 36/14

(52) U.S. Cl. .................. 424/1.81; 424/1.11; 424/1.65; 424/1.85; 424/1.89; 424/9.3; 424/9.37; 544/224; 544/235; 514/247; 514/248

(58) Field of Search ................ 424/1.11, 1.65, 424/1.81, 9.1, 9.3, 9.2, 9.37, 9.4, 1.85, 1.89; 544/224, 235, 233; 514/247, 248, 249, 183

(56) References Cited

U.S. PATENT DOCUMENTS 5,760,041 A * 6/1998 Wissner et al. ............. 514/259
6,251,912 B1 * 6/2001 Wissner et al. ............. 514/259

* cited by examiner

Primary Examiner—Dameron L. Jones
(74) Attorney, Agent, or Firm—G.E. Ehrlich Ltd.

(57) ABSTRACT

Radiolabeled epidermal growth factor receptor tyrosine kinase (EGFR-TK) irreversible inhibitors and their use as biomarkers for medicinal radioimaging such as Positron Emission Tomography (PET) and Single Photon Emission Computed Tomography (SPECT) and as radiopharmaceuticals for radiotherapy are disclosed.

40 Claims, 3 Drawing Sheets

RADIOLABELED IRREVERSIBLE INHIBITORS OF EPIDERMAL GROWTH FACTOR RECEPTOR TYROSINE KINASE AND THEIR USE IN RADIOIMAGING AND RADIOTHERAPY

FIELD AND BACKGROUND OF THE INVENTION

The present invention relates to radiolabeled compounds and their use in radioimaging and/or radiotherapy. More particularly, the present invention relates to radiolabeled irreversible inhibitors of epidermal growth factor receptor tyrosine kinase (EGFR-TK) and their use as biomarkers for medicinal radioimaging such as Positron Emission Tomography (PET) and Single Photon Emission Computed Tomography (SPECT), and as radiopharmaceuticals for radiotherapy.

The use of radioactive nuclides for medicinal purposes is well known in the art. Biologically active compounds that bind to specific cell surface receptors or that in other ways modify cellular functions has received some consideration as radiopharmaceuticals, and therefore, when labeled with a radioactive nuclide, such compounds are used as biospecific agents in radioimaging and radiotherapy.

Positron Emission Tomography (PET), a nuclear medicine imagine technology which allows the three-dimensional, quantitative determination of the distribution of radioactivity within the human body, is becoming an increasingly important tool for the measurement of physiological, biochemical, and pharmacological function at a molecular level, both in healthy and pathological states. PET requires the administration to a subject of a molecule labeled with a positron-emitting nuclide (radiotracer) such as $^{15}O$, $^{13}N$, $^{11}C$ and $^{18}F$, which have half-lives of 2, 10, 20, and 110 minutes, respectively.

Single Photon Emission Computed Tomography (SPECT) is a form of chemical imaging in which emissions from radioactive compounds, labeled with gamma-emitting radionuclides, are used to create cross-sectional images of radioactivity distribution in vivo. SPECT requires the administration to a subject of a molecule labeled with a gamma-emitting nuclide such as $^{99m}Tc$, $^{67}Ga$, $^{111}In$ and $^{123}I$.

Polypeptides such as growth factors, differentiation factors, and hormones often mediate their pleiotropic actions by binding to and activating cell surface receptors with an intrinsic intracellular protein tyrosine kinase activity. Epidermal growth factor receptor-tyrosine kinase (EGFR-TK) is over expressed in breast cancer and other neoplasia. A suitable radiotracer that binds to EGFR-TK might allow, through a nuclear medicine imaging technique such as PET and SPECT, the mapping and quantification of this receptor-kinase. This would allow the study of changes in levels of expression of this receptor, including the monitoring of response to hormonal or other chemotherapy, and could lead to better patient management and differentiation in regard to therapeutic course of action.

Moreover, such radiotracer that comprises a suitable radioactive nuclide can be further used as an EGFR-TK biospecific agent for radiotherapy.

Recently, $^{99m}Tc$-labeled anti EGFR antibody was synthesized and biodistribution and dosimetry studies were performed in humans [1, 2]. However this labeled antibody, similar to other protein radiopharmaceuticals, has high and prolonged retention of radioactivity in the liver which constitutes a major problem for clinical applications. Furthermore, the researchers found that it was difficult to obtain accurate quantification of activity in tumors within normal organs because of varying background activities, particularly in lung lesions where fluid and atelectasis could not be differentiated from tumor.

EGF itself has been labeled for nuclear medicine imaging with gamma emitting nuclides including $^{99m}Tc$ [3, 4] and indium-111 [5, 6], and the positron-emitting nuclide bromine-76 [7, 8]. The biodistribution in normal rats of the latter, bromine-76 EGF (murine), was reported [8], but no other in vivo studies in laboratory animals or humans have been reported.

4-Anilinoquinazolines, also referred to herein as 4-(phenylamino)quinazolines, have been shown to potently and selectively inhibit EGFR-TK activity by binding reversibly to an inner membrane ATP binding site on EGFR-TK, the prototype for such compounds being the small-molecules PD 153035 [9] and AG 1478 [10]. A report of a radioiodinated analog of PD 153035 including in vitro binding studies in MDA-486 cells has been presented [11]. PD 153035 labeled with carbon-11 in the 6,7-methoxy groups has been evaluated in rats implanted with human neuroblastoma xenografts (SH-SY5Y) but specific uptake was not determined in a blocking study [12]. PD 153035 was also labeled with carbon-11 specifically in the 7-methoxy position and biodistribution experiments were performed in normal mice, but uptake specificity could not be demonstrated as administration of an enzyme-blocking dose of PD 153035 caused an increase in tracer uptake in the tissues studied [13]. The same abstract reported the labeling of the 7-(2-fluoroethoxy) PD 153035 analog with fluorine-18, but no biological experiments with this tracer were described. Additionally, the 2-$^{18}F$-fluoroethyl group might be subject to a high rate of $^{18}F$-hydrogen fluoride elimination to give the corresponding alkene ether, potentially resulting in high uptake of fluorine-18 in bone, giving poor in vivo images. Further, these ultra potent ($IC_{50}$<30 pM) inhibitors may only measure flow or permeability surface area rather than biochemical changes [14].

U.S. Pat. No. 6,126,917 teaches 4-(anilino)quinazoline derivatives, reversible inhibitors of EGFR-TK, labeled with fluorine-18 on the aniline ring. These compounds were tested in vitro, in vivo and by PET image analysis. While some of these compounds showed effective (reversible) inhibition activity in vitro, they were found to be ineffective as tracers for the imaging of EGFR-TK in vivo due to kinetic factors such as $k_{on}$ and $k_{off}$ and rapid blood clearance, as was further demonstrated by an animal PET comparative study between fluorine-18 FDG and these radiolabeled compounds. It is assumed that the discrepancy between the encouraging in vitro results and the discouraging in vivo results derives from the ATP competition at the compounds' binding site.

Thus, in order to achieve better imaging results, the non-specific binding of the radiolabeled compounds should be reduced. This can potentially be achieved by the use of derivatives of irreversible EGFR-TK inhibitors that are labeled with a positron-emitting nuclide. The irreversible binding of such compounds could potentially result in higher diagnostic performance. Furthermore, such irreversible inhibitors, when labeled with a suitable radioactive nuclide, can be used as effective radiotherapy agents as well, based on their high affinity toward, and irreversible binding to, tumor cells expressing EGFR-TK. Thus, such radiolabeled compounds that are targeted to the EGF receptor can bind preferentially to tumor cells and would lead to a high effective concentration of the radionuclides and therefore cause preferential cell killing at the site of the tumor.

Irreversible EGFR-TK inhibitors were recently described [15, 16 and U.S. Pat. Nos. 6,153,617 and 6,127,374]. The irreversible binding thereof is achieved by 4-(anilino) quinazoline derivatives that are substituted at the 6 or 7 position of the quinazoline ring with an α,β-unsaturated carboxylic group, preferably an acrylamide group, which binds covalently to the Cys-773 at the EGFR-TK ATP binding site. Some of these compounds showed high potency toward EGFR inhibition in both in vitro and in vivo experiments. However, these compounds were not radiolabeled, and therefore cannot be used for radioimaging or radiotherapy.

There is thus a widely recognized need for, and it would be highly advantageous to have, radiolabeled irreversible inhibitors of EGFR-TK for use in radioimaging and radiotherapy.

SUMMARY OF THE INVENTION

According to the present invention there are provided novel radiolabeled compounds that are irreversible inhibitors of EGFR-TK and methods of using same in radioimaging and radiotherapy.

Thus, according to one aspect of the present invention there is provided a radiolabeled compound of a formula:

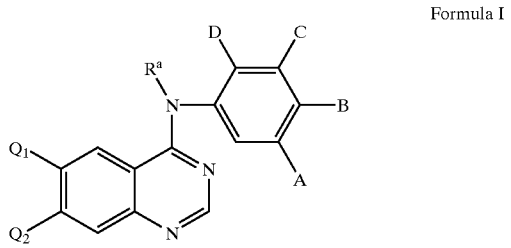

Formula I

Wherein:

Q1 is X—Y(=O)—Z and Q2 is selected from the group consisting of hydrogen, halogen, alkoxy, hydroxy, thiohydroxy, thioalkoxy, alkylamino and amino, or Q1 is selected from the group consisting of hydrogen, halogen, alkoxy, hydroxy, thiohydroxy, thioalkoxy, alkylamino and amino and Q2 is X—Y(=O)—Z;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;

Y is selected from the group consisting of a non-radioactive carbon and a radioactive carbon;

Z is selected from the group consisting of —R$^2$C=CHR$^3$, —C≡C—R$^3$ and —R$^2$C=C=CHR$^3$;

R$^a$ is selected from the group consisting of hydrogen or alkyl having 1–8 carbon atoms;

A, B, C and D are each independently selected from the group consisting of hydrogen, a non-radioactive derivatizing group and a radioactive derivatizing group selected from a radioactive bromine, a radioactive iodine and a radioactive fluorine;

R$^1$ is selected from the group consisting of hydrogen and substituted or non-substituted alkyl having 1–6 carbon atoms;

R$^2$ is selected from the group consisting of hydrogen, halogen and alkyl having 1–6 carbon atoms; and R$^3$ is selected from the group consisting of hydrogen, halogen, carboxy, alkenyl, alkoxy carbonyl, substituted or non-substituted alkyl having 1–6 carbon atoms and substituted or non-substituted phenyl;

provided that the compound comprises at least one radioactive atom.

According to further features in preferred embodiments of the invention described below, the non-radioactive derivatizing group is selected from the group consisting of hydrogen, halogen, alkyl, haloalkyl, hydroxy, alkoxy, carboxy, carbalkoxy, thiohydroxy, thiocarboxy, thioalkoxy, alkylsulfinyl, alkylsulfonyl, amino, diamino, carbamyl, dicarbamoyl, nitro and cyano.

According to still further features in the described preferred embodiments Q1 is X—Y(=O)—Z and Q2 is selected from the group consisting of hydrogen, halogen, alkoxy, hydroxy, thiohydroxy, thioalkoxy, alkylamino and amino.

According to still further features in the described preferred embodiments Q1 is X—Y(=O)—Z and Q2 is hydrogen.

According to still further features in the described preferred embodiments X is —NR$^1$— and Z is —R$^2$C=CHR$^3$.

According to still further features in the described preferred embodiments each of R$^1$, R$^2$ and R$^3$ is hydrogen.

According to still further features in the described preferred embodiments Y is a radioactive carbon.

According to still further features in the described preferred embodiments at least one of A, B, C and D is a radioactive fluorine.

According to still further features in the described preferred embodiments D is a radioactive fluorine.

According to still further features in the described preferred embodiments D is a radioactive fluorine, A and B are each chlorine and C is hydrogen.

According to still further features in the described preferred embodiments A is a radioactive bromine or a radioactive iodine.

According to still further features in the described preferred embodiments the radioactive carbon is carbon-11.

According to still further features in the described preferred embodiments Y is carbon-11, A and B are each chlorine, C is hydrogen and D is fluorine.

According to still further features in the described preferred embodiments the radioactive fluorine is fluorine-18.

According to still further features in the described preferred embodiments the radioactive bromine is bromine-76 or bromine-77.

According to still further features in the described preferred embodiments the radioactive iodine is iodine-123 or iodine-124.

According to another aspect of the present invention there is provided a pharmaceutical composition comprising as an active ingredient the radiolabeled compound of the invention and a pharmaceutical acceptable carrier.

According to yet another aspect of the present invention there is provided a method of monitoring the level of epidermal growth factor receptor within a body of a patient comprising (a) administering to the patient the radiolabeled compound of the invention; and (b) employing a nuclear imaging technique for monitoring a distribution of the compound within the body or within a portion thereof.

According to still further features in the described preferred embodiments the technique is positron emission tomography or single photon emission computed tomography.

According to still another aspect of the present invention there is provided a method of radiotherapy comprising administering to a patient a therapeutically effective amount of the radiolabeled compound of the invention.

According to an additional aspect of the present invention there is provided a method of synthesizing a radiolabeled compound of a formula:

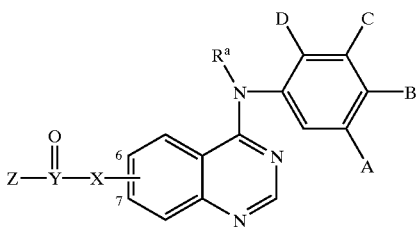

Formula II

Wherein:
X—Y(=O)—Z is at position 6 or 7 of the quinazoline ring;
X is selected from the group consisting of —NR$^1$—, —O—, —NH—NR$^1$—, —O—NR$^1$—, NH—CHR$^1$—, CHR$^1$—NH—, —CHR$^1$—O—, —O—CHR$^1$—, —CHR$^1$—CH$_2$— and —CHR$^1$—S— or absent;
Y is carbon-11;
Z is selected from the group consisting of —R$^2$C=CHR$^3$, —C≡C—R$^3$ and —R$^2$C=C=CHR$^3$;
R$^a$ is selected from the group consisting of hydrogen or alkyl having 1–8 carbon atoms;
A, B, C and D are each independently selected from the group consisting of hydrogen and a non-radioactive derivatizing group;
R$^1$ is selected from the group consisting of hydrogen, and substituted or non-substituted alkyl having 1–6 carbon atoms;
R$^2$ is selected from the group consisting of hydrogen, halogen and alkyl having 1–6 carbon atoms; and
R$^3$ is selected from the group consisting of hydrogen, halogen, carboxy, alkenyl, alkoxy carbonyl, substituted or non-substituted alkyl having 1–6 carbon atoms and substituted or non-substituted phenyl.

The method comprising: (a) coupling an aniline derivatized by the R$^a$, A, B, C and D with a 4-chloroquinazoline substituted at position 6 or 7 by a reactive group, so as to produce a reactive 4-(phenylamino)quinazoline derivatized by the R$^a$, A, B, C and D; and (b) reacting the reactive 4-(phenylamino)quinazoline with a reactive carbon-11 labeled α,β-unsaturated carboxylic derivative.

According to still further features in the described preferred embodiments the X—Y(=O)—Z group is at position 6 of the quinazoline ring.

According to still further features in the described preferred embodiments the reactive 4-(phenylamino) quinazoline is 4-(phenylamino)-6-nitroquinazoline, and the method further comprising, prior to step (b), reducing the 4-(phenylamino)-6-nitroquinazoline so as to produce a 4-(phenylamino)-6-aminoquinazoline derivatized by the A, B, C and D.

According to still further features in the described preferred embodiments the reactive carbon-11 labeled α,β-unsaturated carboxylic derivative is carbon-11 labeled acryloyl chloride.

According to yet an additional aspect of the present invention there is provided a method of synthesizing a radiolabeled compound of formula II as described hereinabove, wherein:
X—Y(=O)—Z is at position 6 or 7 of the quinazoline ring;

X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$—S— or absent;
Y is a non-radioactive carbon;
Z is selected from the group consisting of —R$^2$C=CHR$^3$, —C≡C—R$^3$ and —R$^2$C=C=CHR$^3$;
R$^a$ is selected from the group consisting of hydrogen or alkyl having 1–8 carbon atoms;
A, B, C and D are each independently selected from the group consisting of (i) hydrogen, (ii) a non-radioactive derivatizing group and (iii) fluorine-18, provided that at least one of A, B, C and D is fluorine-18;
R$^1$ is selected from the group consisting of hydrogen, and substituted or non-substituted alkyl having 1–6 carbon atoms;
R$^2$ is selected from the group consisting of hydrogen, halogen and alkyl having 1–6 carbon atoms; and
R$^3$ is selected from the group consisting of hydrogen, halogen, carboxy, alkenyl, alkoxy carbonyl, substituted or non-substituted alkyl having 1–6 carbon atoms and substituted or non-substituted phenyl.

The method comprising: (a) preparing a fluorine-18 labeled aniline derivatized by the R$^a$, A, B, C and D, wherein at least one of A, B, C and D is fluorine-18; (b) coupling the fluorine-18 labeled aniline derivatized by the R$^a$, A, B, C and D with 4-chloroquinazoline substituted at position 6 or 7 by a reactive group, so as to produce a reactive fluorine-18 labeled 4-(phenylamino)quinazoline derivatized by the A, B, C and D; and (c) reacting the reactive fluorine-18 labeled 4-(phenylamino)quinazoline with a reactive α,β-unsaturated derivative.

According to still further features in the described preferred embodiments the reactive fluorine-18 labeled 4-(phenylamino)-quinazoline is fluorine-18 labeled 4-(phenylamino)-6-nitroquinazoline and the method further comprising, prior to step (c), reducing the fluorine-18 labeled 4-(phenylamino)-6-nitroquinazoline so as to produce a fluorine-18 labeled 4-(phenylamino)-6-aminoquinazoline derivatized by the A, B, C and D.

According to still an additional aspect of the present invention there is provided a method of synthesizing a radiolabeled compound of formula II as described hereinabove, wherein:
X—Y(=O)—Z is at position 6 or 7 of the quinazoline ring;
X is selected from the group consisting of —NR$^1$—, —O—, —NH—NR$^1$—, —O—NR$^1$—, NH—CHR$^1$—, —CHR$^1$—NH—, —CHR$^1$—O—, —O—CHR$^1$—, —CHR$^1$—CH$_2$— and —CHR$^1$S— or absent;
Y is a non-radioactive carbon;
Z is selected from the group consisting of —R$^2$C=CHR$^3$, —C=C—R$^3$ and —R$^2$C=C=CHR$^3$;
R$^a$ is selected from the group consisting of hydrogen or alkyl having 1–8 carbon atoms;
A, B, C and D are each independently selected from the group consisting of (i) hydrogen, (ii) a non-radioactive derivatizing group and (iii) a radioactive atom selected from a radioactive bromine and a radioactive iodine, provided that at least one of A, B, C and D is a radioactive bromine or a radioactive iodine;
R$^1$ is selected from the group consisting of hydrogen, and substituted or non-substituted alkyl having 1–6 carbon atoms;
R$^2$ is selected from the group consisting of hydrogen, halogen and alkyl having 1–6 carbon atoms; and R³ is selected from the group consisting of hydrogen, halogen, carboxy, alkenyl, alkoxy carbonyl, substituted or non-substituted alkyl having 1–6 carbon atoms and substituted or non-substituted phenyl.

The method comprising: (a) coupling an aniline derivatized by the Rᵃ, A, B, C and D, wherein at least one of A, B, C and D is a halogen atom, with 4-chloroquinazoline substituted at position 6 or 7 by a reactive group, so as to produce a reactive 4-(phenylamino)quinazoline derivatized by the A, B, C and D; (b) radiolabeling the reactive 4-(phenylamino)quinazoline derivatized by the A, B, C and D with a radioactive bromine or a radioactive iodine, so as to produce a radioactive bromine labeled or a radioactive iodine labeled reactive 4-(phenylamino)quinazoline derivatized by the A, B, C and D, wherein at least one of the A, B, C and D is a radioactive bromine or a radioactive iodine; and (c) reacting the radioactive bromine labeled or radioactive iodine labeled reactive 4-(phenylamino)quinazoline with a reactive α,β-unsaturated derivative.

According to still further features in the described preferred embodiments the reactive 4-(phenylamino)quinazoline is 4-(phenylamino)-6-nitroquinazoline and the method further comprising, prior to step (b), reducing the 4-(phenylamino)-6-nitroquinazoline, so as to produce a 4-(phenylamino)-6-aminoquinazoline derivatized by the A, B, C and D, wherein at least one of the A, B, C and D is a halogen.

According to still further features in the described preferred embodiments the halogen is bromine.

The present invention successfully addresses the shortcomings of the presently known configurations by providing novel irreversible biomarkers for radioimaging and radiopharmaceuticals for radiotherapy.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
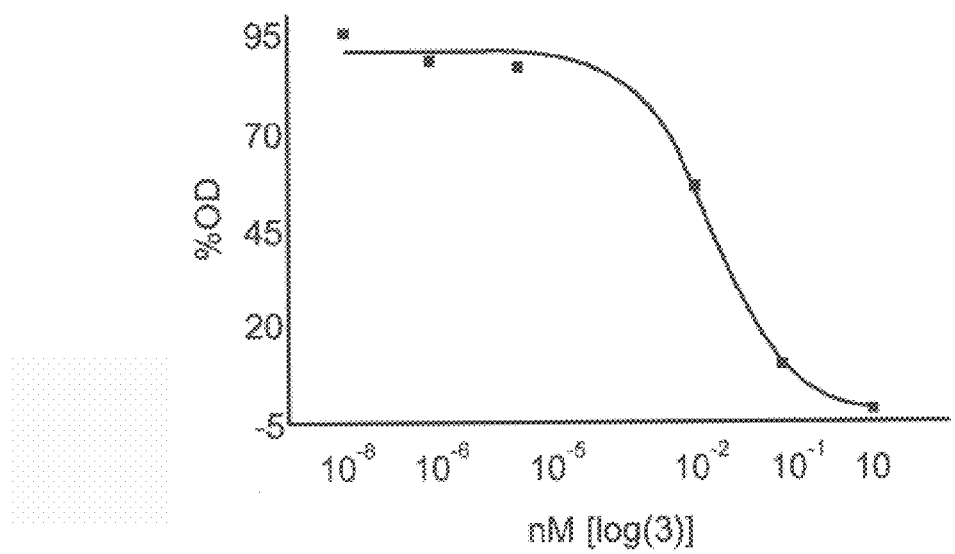
FIG. 1 presents an example of dose-response autophosphorylation inhibition curve for Compound 3 of the invention with an IC$_{50}$ value of 0.051 nM and a range of 0.0088/0.294 as 95% confidence interval.

The present invention is of novel radiolabeled compounds which can be used as biomarkers for radioimaging such as Positron Emission Tomography (PET) and Single Photon Emission Computed Tomography (SPECT) and as radiopharmaceuticals for radiotherapy. Specifically, the novel radiolabeled compounds can be used as irreversible PET or SPECT biomarkers and/or as radiopharmaceuticals, for quantification, mapping and radiotherapy of epidermal growth factor receptor tyrosine kinase (EGFR-TK) associated diseases, such as a variety of cancers in which amplification, mutation and/or overexpression of EGFR-TK has occured.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a radiolabeled compound of a formula:

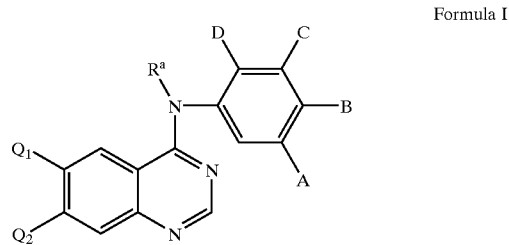

Formula I

Wherein:

Q1 is X—Y(=O)—Z and Q2 is selected from the group consisting of hydrogen, halogen, alkoxy, hydroxy, thiohydroxy, thioalkoxy, alkylamino and amino, or Q1 is selected from the group consisting of hydrogen, halogen, alkoxy, hydroxy, thiohydroxy, thioalkoxy, alkylamino and amino and Q2 is X—Y(=O)—Z;

X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;

Y is selected from the group consisting of a non-radioactive carbon and a radioactive carbon;

Z is selected from the group consisting of —R²C=CHR³, —C≡C—R³ and —R²C=C=CHR³;

Rᵃ is selected from the group consisting of hydrogen or alkyl having 1–8 carbon atoms;

A, B, C and D are each independently selected from the group consisting of hydrogen, a non-radioactive derivatizing group and a radioactive derivatizing group selected from a radioactive bromine, a radioactive iodine and a radioactive fluorine;

$R^1$ is selected from the group consisting of hydrogen and substituted or non-substituted alkyl having 1–6 carbon atoms;

$R^2$ is selected from the group consisting of hydrogen, halogen and alkyl having 1–6 carbon atoms; and $R^3$ is selected from the group consisting of hydrogen, halogen, carboxy, alkenyl, alkoxy carbonyl, substituted or non-substituted alkyl having 1–6 carbon atoms and substituted or non-substituted phenyl;

with the provision that the compound comprises at least one (e.g., one, two or more) radioactive atom.

As used herein in the specification and in the claims section that follows, the phrase "radiolabeled compound" or "radioactive atom" (type specified or not) refer to a compound that comprises one or more radioactive atoms or to a radioactive atom with a specific radioactivity above that of background level for that atom. It is well known, in this respect, that naturally occurring elements are present in the form of varying isotopes, some of which are radioactive isotopes. The radioactivity of the naturally occurring elements is a result of the natural distribution of these isotopes, and is commonly referred to as a background radioactive level. However, there are known methods of enriching a certain element with isotopes that are radioactive. The result of such enrichment is a population of atoms characterized by higher radioactivity then a natural population of that atom, and thus the specific radioactivity thereof is above the background level.

Thus, the radiolabeled compounds of the present invention have a specific radioactivity that is higher than the corresponding non-labeled compounds, and can therefore be used as agents for radioimaging and radiotherapy.

Furthermore, the term "non-radioactive", as used herein with respect to an atom or a derivatizing group, refers to an atom or a derivatizing group that does not comprise a radioactive atom and thus the specific radioactivity thereof is of a background level.

The term "radioactive", as used herein with respect to an atom or a derivatizing group, refers to an atom or a derivatizing group that comprise a radioactive atom and therefore the specific radioactivity thereof is above the background level.

As used herein in the specification and in the claims section that follows, the term "derivatizing group" refers to a major portion of a group which is covalently attached to another group.

As used herein in the specification and in the claims section that follows, the term "halogen", which is also referred to herein as "halo", refers to fluorine, chlorine, bromine or iodine.

As used herein, the term "hydroxy" refers to an —OH group.

The term "alkoxy" refers to both an —O-alkyl and an —O-cycloalkyl group, as defined hereinbelow. Representative examples of alkoxy groups include methoxy, ethoxy, propoxy and tert-butoxy.

As used herein, the term "alkyl" refers to a saturated aliphatic hydrocarbon including straight chain and branched chain groups. Preferably, the alkyl group is a medium size alkyl having 1 to 10 carbon atoms. More preferably, it is a lower alkyl having 1 to 6 carbon atoms. Most preferably it is an alkyl having 1 to 4 carbon atoms. Representative examples of an alkyl group are methyl, ethyl, propyl, isopropyl, butyl, tert-butyl, pentyl and hexyl.

The alkyl group, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, perhalo, trihalomethyl, carboxy, alkoxycarbonyl, thiocarboxy, carbamyl, cyano, nitro, N-piperidinyl, N-piperazinyl, $N_1$-piperazinyl-$N_4$-alkyl, N-pyrrolidyl, pyridinyl, N-imidazoyl, N-morpholino, N-thiomorpholino, N-hexahydroazepine, amino or NRbRc, wherein Rb and Rc are each independently hydrogen, alkyl, hydroxyalkyl, N-piperidinyl, N-piperazinyl, $N_1$-piperazinyl-$N_4$-alkyl, N-pyrrolidyl, pyridinyl, N-imidazoyl, N-morpholino, N-thiomorpholino and N-hexahydroazepine.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane.

The term "thiohydroxy" refers to a —SH group.

The term "thioalkoxy" refers to both an —S-alkyl group, and an —S-cycloalkyl group, as defined herein.

The term "amino" refers to an —$NH_2$ group.

The term "alkylamino" refers to a —NRbRc group as defined hereinabove.

The term "carboxy" refers to a —C(=O)— group.

The term "alkoxycarbonyl" group, also referred to herein as "carbalkoxy", refers to a —C(=O)—O—R' group, where R' is alkyl, cycloalkyl, alkenyl, aryl, heteroaryl (bonded through a ring carbon) or heteroalicyclic (bonded through a ring carbon) as defined hereinabove.

An "alkenyl" group refers to an alkyl group which consists of at least two carbon atoms and at least one carbon—carbon double bond.

An "aryl" group refers to an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl.

A "phenyl" group, according to the present invention can be substituted by one to three substituents or non-substituted. When substituted, the substituent group may be, for example, halogen, alkyl, alkoxy, nitro, cyano, trihalomethyl, alkylamino or monocyclic heteroaryl.

A term "heteroaryl" group includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system.

An "aryloxy" group refers to both an —O-aryl and an —O-heteroaryl group, as defined herein.

An "thioaryloxy" group refers to both an —S-aryl and an —S-heteroaryl group, as defined herein.

A "trihalomethyl" group refers to a —CX$_3$ group, wherein X is a halogen as defined herein. A representative example of a trihalomethyl group is a —CF$_3$ group.

A "perhalo" group refers to a group in which all the hydrogen atoms thereof have been replaced by halogen atoms.

A "thiocarboxy" group refers to a —C(=S)—R' group, where R' is as defined herein.

An "alkylsulfinyl" group refers to an —S(=O)—R' group, where R' is as defined herein.

An "alkylsulfonyl" group refers to an —S(=O)$_2$—R' group, where R' is as defined herein.

A "carbamyl" group refers to an —OC(=O)—NRbRc group, where Rb and Rc are as defined herein.

A "nitro" group refers to a —NO$_2$ group.

A "cyano" group refers to a —C≡N group.

The radiolabeled compounds of the present invention are derivatized 4-(phenylamino)quinazolines that are substituted at position 6 or 7 of the quinazoline ring by an α,β-unsaturated carboxylic group, also defined herein as a X—Y(=O)—Z group.

As used herein in the specification and in the claims section that follows, the term "α,β-unsaturated carboxylic group" refers to any group that comprise a —C(=O)— group and is linked at the distal end thereof to an unsaturated group. The carboxylic group can be, for example, an amide, an ester, a hydrazinamide or a ketone.

The term "unsaturated group" refers to a substituted or non-substituted hydrocarbon that comprise at least two carbon atoms and at least one unsaturated bond. Representative examples of an unsaturated group include alkenyl, alkynyl and diene.

This class of derivatized 4-(phenylamino)quinazolines is known to bind irreversibly to the ATP site of EGFR-TK due to the α,β-unsaturated carboxylic group attached to the anilinoquinazoline ring [15, 16 and U.S. Pat. Nos. 6,153,617 and 6,127,374]. The α,β-unsaturated carboxylic group was found to covalently attach to the Cys-773 at the EGFR-TK ATP binding site, and thus acts as a Michael acceptor.

Prior to the disclosure of this class of compounds, derivatized 4-(phenylamino)quinazolines were known to bind irreversibly to the EGFR-TK ATP site. The level of the biological activity of these compounds is influenced by the nature of the derivatizing groups at the anilino ring thereof. However, the covalent binding to the receptor which is effected by the α,β-unsaturated carboxylic group attached to this class of quinazolines, enables the use of 4-(phenylamino)quinazolines that are derivatized by various derivatizing groups as EGFR-TK inhibitors.

Thus, according to a preferred embodiment of the present invention, the non-radioactive derivatizing group of the radiolabeled compound of the present invention is, for example, hydrogen, halogen, alkyl, haloalkyl, hydroxy, alkoxy, carboxy, carbalkoxy, thiohydroxy, thiocarboxy, thioalkoxy, alkylsulfinyl, alkylsulfonyl, amino, diamino, carbamyl, dicarbamoyl, nitro and cyano.

According to another preferred embodiment of the present invention, the X—Y(=O)—Z group of the radiolabeled compound is attached to position 6 of the quinazoline ring. A 6-position α,β-unsaturated carboxylic group has higher binding potency to the EGFR-TK ATP site [15, 16 and U.S. Pat. Nos. 6,153,617 and 6,127,374].

According to still another preferred embodiment of the invention, the 6-position α,β-unsaturated carboxylic group is an acrylamide group. Thus, a preferred radiolabeled compound according to the present invention is a radiolabeled [4-(phenylamino)quinazolin-6-yl]acrylamide derivatized by the R$^a$, A, B, C and D as these symbols are defined above.

U.S. Pat. No. 6,126,917 further teaches that 4-(phenylamino)quinazolines that are derivatized at position 6 of the anilino group by fluorine are potent inhibitors of EGFR-TK. The highest affinity toward the receptor is achieved using 4-[(3,4-dichloro-6-fluorophenyl)-amino] quinazolines.

According to a preferred embodiment of the invention Y is a carbon, X is —NH, Z is CH$_2$=CH—, R$^a$ is hydrogen, A and B are each chlorine, C is hydrogen and D is fluorine, which is referred to hereinbelow as Compound 3.

According to another preferred embodiment of the invention, Y is a radioactive carbon, and the radioactive carbon is carbon-11.

According to still another preferred embodiment of the invention, at least one of A, B, C and D is a radioactive fluorine, and the radioactive fluorine is fluorine-18. Preferably, D is fluorine-18.

Thus, according to a presently most preferred embodiment of the invention, in Compound 3, Y is carbon-11.

According to another presently preferred embodiment of the invention, in Compound 3, D is fluorine-18.

Further according to preferred embodiments of the invention the radioactive atom is radioactive bromine such as bromine-76 and bromine-77. Preferably, A is the radioactive bromine. A bromine-76 labeled compound of the invention can be used for PET radioimaging, while a bromine-77 labeled compound of the invention can be used for radiotherapy.

According to another preferred embodiments of the present invention the radioactive atom is radioactive iodine such as iodine-123 or iodine-124. Preferably, A is the radioactive iodine. An iodine-123 labeled compound of the invention can be used for SPECT radioimaging, while an iodine-124 labeled compound of the invention can be used for both PET radioimaging and/or radiotherapy.

Radiosyntheses:

According to another aspect of the present invention, there are provided methods for the syntheses of the radiolabeled compounds of the invention.

The radiolabeling of the compounds can be performed using three alternative strategies as follows:

The first strategy involves the incorporation of fluorine-18 atom within the aniline ring and therefore requires that the radiolabeling be the first step of a total of five-step radiosynthesis, as is further exemplified in the Examples section that follows.

The second strategy for radiolabeling according to the present invention involves the incorporation of a carbon-11 atom within the α,β-unsaturated carboxylic group which is reacted at the final step of the synthesis, thus being an advantageous one-step radiosynthesis.

The third strategy involves the incorporation of radioactive bromine or radioactive iodine within the anilino ring of the 4-(phenylamino)quinazoline, prior to the final step of the synthesis, resulting in an advantageous two-step radiosynthesis, wherein the final step is simple to perform (see below).

Thus, according to still another aspect of the present invention, there is provided a method of synthesizing a carbon-11 labeled compound as is described hereinabove. The method is effected by coupling an aniline derivatized by R$^a$, A, B, C and D with a 4-chloroquinazoline substituted at position 6 or 7 by a reactive group, so as to produce a reactive 4-(phenylamino)quinazoline derivatized by the R$^a$, A, B, C and D, and reacting the reactive 4-(phenylamino) quinazoline with a reactive carbon-11 labeled α,β-unsaturated carboxylic derivative.

As used herein in the specification and in the claims section that follows, the term "reactive" with respect to a group or a derivative refers to a group or derivative which can be easily reacted with another group so as to produce a new compound that comprises a new functional group. Representative examples of a reactive group include nitro, amino, hydroxyl and halogen. A carboxylic acid chloride is a representative example of a reactive derivative.

In one particular, 3,4-dichloro-6-fluoroaniline is reacted with 4-chloro-6-nitroquinazoline, so as to produce 4-[(3,4-dichloro-6-fluorophenyl)amino]-6-nitroquinazoline, which is reduced, by means of an ethanolic solution of hydrazine hydrate and Raney®Nickel, so as to produce 4-[(3,4-dichloro-6-fluorophenyl)amino]-6-aminoquinazoline. Then, the 4-[(3,4-dichloro-6-fluorophenyl)amino]-6-aminoquinazoline is reacted with a carbon-11 labeled acryloyl chloride so as to produce a carbon-11 labeled {4-[(3,4-dichloro-6-fluorophenyl)amino]quinazoline-6-yl] acrylamide (radiolabeled Compound 3).

According to yet another aspect of the present invention, there is provided a method of synthesizing a fluorine-18 labeled compound as is described hereinabove. The method is effected by preparing a fluorine-18 labeled aniline derivatized by the A, B, C and D by means of reacting a pre-selected nitrobenzene with a $^{18}$F-fluoride ion and thereafter reducing the fluoronitrobenzene obtained, by means of an ethanolic solution of hydrazine hydrate and Raney®Nickel. Then, coupling the derivatized fluorine-18 labeled aniline with 4-chloroquinazoline substituted at position 6 or 7 by a reactive group as defined herein, so as to produce a reactive fluorine-18 labeled 4-(phenylamino) quinazoline derivatized by the A, B, C and D, and reacting the reactive fluorine-18 labeled 4-(phenylamino)quinazoline with a reactive α,β-unsaturated carboxylic derivative.

In one particular, fluorine-18 labeled 3,4-dichloro-6-fluoroaniline is prepared by reacting 1,2-dichloro-4,5-dinitrobenzene with $^{18}$F-fluoride ion and reducing the obtained fluorine-18 labeled 3,4-dichloro-6-fluoronitrobenzene as described hereinabove. The fluorine-18 labeled aniline is then reacted with 4-chloro-6-nitroquinazoline, and the obtained fluorine-18 labeled 4-[(3,4-dichloro-6-fluorophenyl)amino]-6-nitroquinazoline is reduced thereafter, by means of an ethanolic solution of hydrazine hydrate and Raney®Nickel, so as to produce fluorine-18 labeled 4-[(3,4-dichloro-6-fluorophenyl)amino]-6-aminoquinazoline, which is reacted with an acryloyl chloride so as to produce a fluorine-18 labeled {4-[(3,4-dichloro-6-fluorophenyl)amino]quinazoline-6-yl}acrylamide (radiolabeled Compound 3).

According to still another aspect of the present invention, there is provided a method of synthesizing a radioactive bromine labeled or a radioactive iodine labeled compound as is described hereinabove. The method is effected by coupling an aniline derivatized by R$^a$, A, B, C and D, wherein at least one of A, B, C and D is a halogen, with 4-chloroquinazoline substituted at position 6 or 7 by a reactive group as defined herein, so as to produce a reactive 4-(phenylamino)quinazoline derivatized by the A, B, C and D as defined herein, and radiolabeling the reactive 4-(phenylamino)quinazoline by means of reacting the reactive 4-(phenylamino)quinazoline derivatized by the A, B, C and D, with bistributyltin, using tetrakis (triphenylphosphine)palladium as catalyst, so as to produce a reactive 4-(phenylamino)quinazoline derivatized by the A, B, C and D, wherein at least one of A, B, C and D is tributyltin, and thereafter reacting the stanylated product with a radioactive bromine or a radioactive iodine, in the presence of an oxidizing agent, so as to produce a reactive radioactive bromine labeled or radioactive iodine labeled 4-(phenylamino)quinazoline. Then, reacting the reactive radioactive bromine labeled or radioactive iodine labeled 4-(phenylamino)quinazoline with a reactive α,β-unsaturated carboxylic derivative.

In one particular, 3-bromoaniline is reacted with 4-chloro-6-nitroquinazoline to produce 4-[(3-bromophenyl)amino]-6-nitro quinazoline, which is reduced thereafter, by means of an ethanolic solution of hydrazine hydrate and Raney®Nickel, to the corresponding 6-aminoquinazoline. The 4-[(3-bromophenyl)amino]-6-aminoquinazoline is then reacted with bistributyltin in the presence of tetrakis (triphenylphosphine)palladium in triethylamine solution and the obtained stanylated product is reacted thereafter with bromine-76, as described hereinabove. The obtained bromine-76 labeled 4-[(3-bromophenyl)amino]-6-aminoquinazoline is then reacted with an acryloyl chloride to produce a bromine-76 labeled {4-[(3-bromophenyl) amino]quinazoline-6-yl}acrylamide.

Radioimaging and Radiotherapy:

The radiolabeled compounds herein described can be used as radioimaging and radiotherapy agents. Carbon-11 labeled, fluorine-18 labeled, bromine-76 labeled and iodine-124 labeled compounds of the invention can be used as biomarkers for PET radioimaging, whereas iodine-123 labeled compounds of the invention can be used as biomarkers for SPECT radioimaging. Bromine-77 labeled and iodine-124 labeled compounds of the invention can be used as radiopharmaceuticals for radiotherapy.

Thus, the radiolabeled compounds of the invention can be used to effect a method of monitoring the level of epidermal growth factor receptor within a body of a patient by administering to the patient any of the carbon-11, fluorine-18, bromine-76, iodine-123 or iodine-124 radiolabeled compounds described herein and employing a nuclear imaging technique, such as positron emission tomography or single photon emission computed tomography, for monitoring a distribution of the compound within the body or within a portion thereof.

Nuclear imaging dosing depends on the affinity of the compound to its receptor, the isotope employed and the specific activity of labeling. Persons ordinarily skilled in the art can easily determine optimum nuclear imaging dosages and dosing methodology.

The bromine-77 and iodine-124 radiolabeled compounds herein described can be used to effect a method of radiotherapy by administering to a patient a therapeutically effective amount of a radiolabeled compound as described herein, mixed with, for example, a pharmaceutically acceptable carrier.

For any compound used in the method of the invention, a therapeutically effective amount, also referred to herein as a therapeutically effective dose, can be estimated initially from cell culture assays. For example, a dose can be formulated in animal models to achieve a circulating concentration range that includes the IC$_{50}$ or the IC$_{100}$ as determined in cell culture. Such information can be used to more accurately determine useful doses in humans. Initial dosages can also be estimated from in vivo data. Using these initial guidelines one having ordinary skill in the art could determine an effective dosage in humans.

Moreover, toxicity and therapeutic efficacy of the radiolabeled compounds described herein can be determined by standard pharmaceutical procedures in cell cultures or experimental animals, e.g., by determining the LD$_{50}$ and the ED$_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Pharmaceutical Compositions:

Any of the radiolabeled compounds described herein can be formulated into a pharmaceutical composition which can be used for radiotherapy of a disease or for imaging. Such a composition includes as an active ingredient any of the radiolabeled compounds described herein and a pharmaceutically acceptable carrier.

As used herein a "pharmaceutical composition" refers to a preparation of one or more of the radiolabeled compounds described herein, with other chemical components such as pharmaceutically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water. Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition.

Routes of administration: Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Composition/formulation: Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The radiolabeled compounds described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The radiolabeled compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Additional objects, advantages, and novel features of the present invention will become apparent to one ordinarily skilled in the art upon examination of the following examples, which are not intended to be limiting. Additionally, each of the various embodiments and aspects of the present invention as defined hereinabove and as claimed in the claims section below finds experimental support in the following examples.

EXAMPLES

Reference is now made to the following examples, which together with the above descriptions, illustrate the invention in a non-limiting fashion.

Materials, Syntheses and Experimental Methods
Syntheses
Materials and Methods:

Chemicals were purchased from Sigma Chemical Co. (St. Louis, Mo.), Fisher Scientific (Pittsburgh, Pa.), Aldrich Co. (Milwaukee, Wis.) or Carlo Erba. All the chemicals were used as supplied, except DMSO which was stored over activated molecular sieves for at least one day prior to use. Microwave heating was performed in a conventional oven (BR 740XL, Brother) operating at 500 W (full power).

Generation of [F-18] Fluoride ion: $^{18}$F-Fluoride ion was produced by the $^{18}$O(p, n) $^{18}$F nuclear reaction on about 350 $\mu$l $^{18}$O-enriched water (97% isotopic purity, Rotem, Israel) as a target in the Hadassah-Hebrew University IBA 18/9 cyclotron (Belgium). Reactive organic $^{18}$F-fluoride ion was prepared by adding 10–50 $\mu$l irradiated target water to Kryptofix®2.2.2 (10 mg, 27 $\mu$l) and $K_2CO_3$ (1 mg) in water-acetonitrile. Azeotropic removal of water with acetonitrile was achieved by heating under a stream of nitrogen. The dried Kryptofix®2.2.2—potassium $^{18}$F-fluoride was then dissolved in 300 $\mu$l anhydrous DMSO for use in radiolabeling.

Generation of carbon-11 $CO_2$: carbon-11 $CO_2$ was produced by the $^{14}$N(p, $\alpha$) $^{11}$C nuclear reaction on a mixture of $N_2$/0.5% $O_2$ as a target, in the Hadassah-Hebrew University IBA 18/9 cyclotron (Belgium).

HPLC was performed on a Varian 9012Q pump, a Varian 9050 variable wavelength UV detector operating at 254 nm, and a Bioscan Flow-Count radioactivity detector with a NaI crystal.

Fluorine-18 labeled, radioactive bromine labeled and radioactive iodine labeled compounds of the invention were purified on a normal phase system using a silica column (5 $\mu$m, 250×10 mm, Primesphere, Phenomenex) and the following mobile phase system: hexane-dichloromethane-methanol, 50:48:2; at 10 minutes, gradient to 35:60:5 over 30 minutes; 5 ml/minutes. Eluent fractions (2.5 ml) were collected on a fraction collector (FC205, Gilson). Analysis of formulated radiotracers was performed on a reversed phase system using a C18 column (5 $\mu$m, 250×4.6 mm, Econosil, Alltech) and the following mobile phase system: water-methanol, 20:80; 1 ml/minutes.

Fluorine-18, bromine and iodine radiotracers formulation was performed as follows: Selected semi-preparative eluent fractions were transferred to a glass flask and the solution was concentrated in vacuum to dryness. The residue was dissolved in 0.5 ml EtOH and 0.5 ml isotonic saline. The solution was filtered through an EtOH-wetted Millex-FG filter (0.2 $\mu$m, Millipore), and another 4 ml saline was used to rinse the flask and filter, providing a 5 ml, 10% EtOH, 90% saline formulation.

Carbon-11 labeled compounds were purified on a reverse phase system using a C18-reverse phase-prep column and the following mobile phase system: 48% $CH_3CN$ in 52% acetate buffer (pH=3.8), at 15 ml/minute flow rate. Eluent fractions (2.5 ml) were collected on a fraction collector (FC205, Gilson). Analysis of formulated carbon-11 radiotracers was performed on C18 column $\mu$ Bondapak analytical column, using 40% $CH_3CN$ in 60% acetate buffer (pH=3.8) as elute, at a flow rate of 1.7 ml/min Carbon-11 radiotracer formulation was performed as follows: The product was collected in a vial that contained 50 ml water and 1 ml NaOH (1 M). The solution was passed through a pre-washed (10 ml water) activated C18 cartridge, and washed with 10 ml sterile water. The product was eluted using 1 ml ethanol followed by 5 ml of saline.

General Synthetic Schemes:
Carbon-11 Labeled 4-(phenylamino)quinazolines Substituted by an $\alpha,\beta$-unsaturated Carboxylic Group (Michael Acceptor Side-chain):

A general synthetic pathway for producing carbon-11 labeled 4-(phenylamino)quinazolines substituted by an $\alpha,\beta$-unsaturated carboxylic group, as is presented in Scheme 1, includes the steps of: (i) coupling a derivatized or non-derivatized aniline with 4-chloroquinazoline that is substituted at position 6 or 7 by a reactive group (L, Scheme 1, see examples below), so as to produce a reactive 4-(phenylamino)quinazoline; and (ii) reacting the reactive quinazoline, under the appropriate conditions, with a reactive derivative of a carbon-11 labeled $\alpha,\beta$-unsaturated carboxylic group (X—Y(=O)—M, Scheme 1), so as to produce the carbon-11 labeled 4-(phenylamino)quinazoline substituted at position 6 or 7 thereof by an α,β-unsaturated carboxylic group.

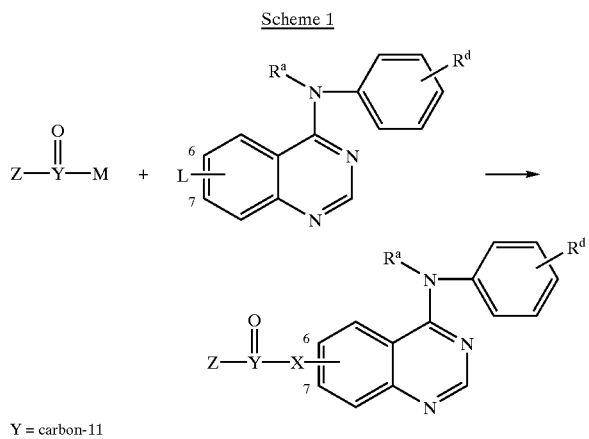

Scheme 1

Y = carbon-11

Thus, according to the general pathway described above (Scheme 1), carbon-11 labeled 4-(phenylamino) quinazolines substituted by the following α,β-unsaturated carboxylic side-chain groups are synthesizable:

Amine-linked side-chains: 4-(phenylamino)quinazoline substituted at position 6 or 7 by a nitro group is reduced to the corresponding amine, which is then acylated by a carbon-11 labeled α,β-unsaturated carboxylic acid in the presence of a coupling agent, such as EI or AC, or by the acid chloride.

Oxygen-linked side-chains: 4-(phenylamino)quinazoline substituted at position 6 or 7 by a methoxy group is cleaved to produce the corresponding hydroxyl compound, which is then acylated either by a carbon-11 labeled α,β-unsaturated carboxylic acid in the presence of a coupling agent such as EDAC, or by the acid chloride.

Carbon-linked side-chains: 4-(phenylamino)quinazoline substituted at position 6 or 7 by iodine is converted to the corresponding arylzinc compound which is coupled with a carbon-11 labeled α,β-unsaturated carboxylic group that comprises an activated halide.

Hydrazino-linked side-chains: 4-(phenylamino) quinazoline substituted at position 6 or 7 by a nitro group is reduced to the corresponding amine, which is diazotized and then reduced to the hydrazine compound. The distal nitrogen of the hydrazine is then acylated, using methods well-known to one skilled in the art, by an appropriate carbon-11 labeled α, β-unsaturated carboxylic derivative.

Hydroxylamino-O-linked side-chains: 4-(phenylamino) quinazoline substituted at position 6 or 7 by a nitro group is reduced under appropriate mildly reducing conditions to the hydroxylamine compound which is then acylated, using methods well-known to one skilled in the art, by an appropriate carbon-11 labeled α,β-unsaturated carboxylic derivative.

Methyleneamino-N-linked side-chains: 4-(phenylamino) quinazoline substituted at position 6 or 7 by a nitro group is reduced to the corresponding amine which is diazotized and then converted to nitrile, preferably in the presence of copper or nickel salt catalysis. The nitrile compound is then reduced to a methylamine compound which is acylated, using methods well-known to one skilled in the art, by an appropriate carbon-11 labeled α,β-unsaturated carboxylic derivative.

Methyleneoxy-O-linked side-chains: 4-(phenylamino) quinazoline substituted at position 6 or 7 by a hydroxymethyl is produced using methods obvious to one skilled in the art. For example, 4-(phenylamino)quinazoline substituted at position 6 or 7 by a nitro group is reduced to the corresponding amine which is diazotized, converted to the nitrile as described above, partially reduced to an imine, hydrolyzed and reduced to the corresponding hydroxymethyl. The hydroxyl group is then acylated, using methods well-known to one skilled in the art, by an appropriate carbon-11 labeled α,β-unsaturated carboxylic derivative.

Ethano-linked side-chains: 4-(phenylamino)quinazoline substituted at position 6 or 7 by iodine is converted, via an organozincate, to the corresponding cuprate. The cuprate is reacted with an appropriately mono-masked carbon-11 labeled divinylketone which is then subjected to unmasking of the remaining unsaturated functionality.

Aminomethyl-C-linked side-chains: 4-(phenylamino) quinazoline substituted at position 6 or 7 by a nitro group is reduced to the corresponding amine which is alkylated by a double-bond protected derivative of carbon-11 labeled 1-bromobut-3-ene-2-one. The protecting group is then removed by methods known to one skilled in the art.

hydroxymethyl-C-linked side-chains: 4-(phenylamino) quinazoline substituted at position 6 or 7 by a methoxy group is cleaved to the corresponding hydroxyl compound which is alkylated by a double-bond protected derivative of carbon-11 labeled 1-bromobut-3-ene-2-one. The protecting group is then removed by methods known to one skilled in the art.

Thiomethyl-C-linked side-chains: 4-(phenylamino) quinazoline substituted at position 6 or 7 by halide is converted to the corresponding mercapto compound which is then alkylated by a double-bond protected derivative of carbon-11 labeled 1-bromobut-3-ene-2-one. The protecting group is then removed by methods known to one skilled in the art.

Fluorine-18 Labeled 4-(phenylamino)quinazolines Having an α,β-unsaturated Carboxylic Side-Chain (Michael Acceptor Side-Chain)

A general synthetic pathway for producing fluorine-18 labeled 4-(phenylamino)quinazolines having an α,β-unsaturated carboxylic side-chain, as is presented in Scheme 2, includes the steps of: (i) preparing a fluorine-18 labeled aniline derivative by reacting a [F-18]fluoride ion with the corresponding dinitrobenzene derivative and then reducing the fluorine-18 labeled fluoronitrobenzene; (ii) reacting the fluorine-18 labeled aniline derivative with 4-chloroquinazoline that is substituted by a reactive group (L, Scheme 2, see examples below), so as to produce a reactive fluorine-18 labeled 4-(phenylamino)quinazoline; and (iii) reacting the reactive fluorine-18 labeled 4-(phenylamino)quinazoline with a reactive derivative of an α,β-unsaturated carboxylic group (X—Y(=O)—M, Scheme 2), so as to produce the fluorine-18 labeled 4-(phenylamino)quinazoline substituted at position 6 or 7 thereof by an α,β-unsaturated carboxylic side-chain.

Scheme 2

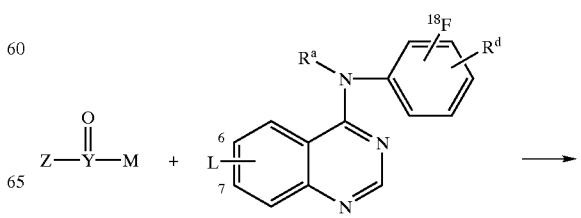

-continued

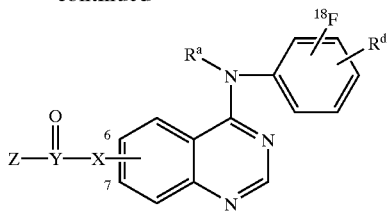

Y = non-radioactive carbon

Thus, fluorine-18 labeled 4-(phenylamino)quinazolines substituted by various α,β-unsaturated carboxylic side-chains can be synthesized according to the general pathway described above. The reactive fluorine-18 labeled 4-(phenylamino)quinazoline can be reacted with the reactive α,β-unsaturated carboxylic derivatives using the methods described hereinabove.

Radioactive Bromine Labeled and Radioactive Iodine Labeled 4-(phenylamino)quinazolines Having an α,β-unsaturated Carboxylic Side-chain (Michael Acceptor Side-chain)

A general synthetic pathway for producing radioactive bromine labeled and radioactive iodine labeled 4-(phenylamino)-quinazolines having an α,β-unsaturated carboxylic side-chain, as is presented in Scheme 3, includes the steps of: (i) coupling an aniline that is derivatized by a halogen with 4-chloroquinazoline that is substituted by a reactive group (L, Scheme 3, see examples below), so as to produce a reactive 4-(phenylamino)quinazoline that is derivatized by a halogen; (ii) radiolabeling the reactive 4-(phenylamino)quinazoline by reacting the 4-(phenylamino)quinazoline that is derivatized by a halogen with bistributyltin, using tetrakis(triphenylphosphine) palladium as catalyst and reacting thereafter the obtained stanylated product with a radioactive bromine or a radioactive iodine, in the presence of an oxidizing agent, so as to produce a reactive radioactive bromine labeled or radioactive iodine labeled 4-(phenylamino)quinazoline; and (iii) reacting the reactive radioactive bromine labeled or radioactive iodine labeled 4-(phenylamino)quinazoline with a reactive derivative of an α,β-unsaturated carboxylic group (X—Y(=O)—M, Scheme 3), so as to produce the radioactive bromine labeled or radioactive iodine labeled 4-(phenylamino)-quinazoline substituted at position 6 or 7 thereof by an α,β-unsaturated carboxylic side-chain.

Scheme 3

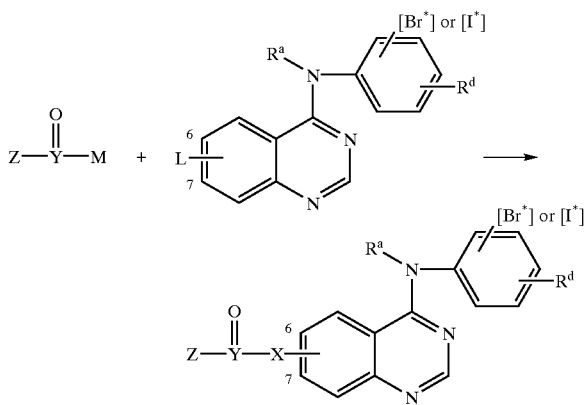

Y = non-radioactive carbon
[Br*] or [I*] = radioactive bromine or iodine

The radioactive bromine can be bromine-76 or bromine-77, and the radioactive iodine can be iodine-123 or iodine-124.

Thus, 4-(phenylamino)quinazolines that are radiolabeled by bromine-76, bromine-77, iodine-123 or iodine-124 and substituted by various α,β-unsaturated carboxylic side-chains can be synthesized according to the general pathway described above. The reactive radioactive bromine labeled or radioactive iodine labeled 4-(phenylamino)quinazoline can be reacted with the reactive α,β-unsaturated carboxylic derivatives using the methods described hereinabove.

Synthesis of α,β-unsaturated [4-(phenylamino)-quinazolin-6-yl]amides—General Procedure:

(i) Aniline or derivatized aniline (1 equivalent) is reacted with 4-chloro-6-nitroquinazoline (3.5 equivalents), in a polar solvent such as iso-propylalcohol. The product, 4-(phenylamino)-6-nitroquinazoline, is obtained after filtration.

(ii) A solution of 4-(phenylamino)-6-nitroquinazoline in ethanol/water and a polar solvent such as iso-propylalcohol is reacted at reflux temperature with hydrazine hydrate and Raney®Nickel. The reaction mixture is filtered, evaporated and purified by silica gel chromatography, to give the product, 4-(phenylamino)-6-aminoquinazoline.

(iii) 4-(phenylamino)-6-aminoquinazoline is reacted with α,β-unsaturated acyl chloride at 0° C. in THF to give the final product in quantitative yield.

Synthesis of {4-[(3,4-dichloro-6-fluorophenyl)amino] quinazoline-6-yl}acrylamide (Compound 3)

(i) 3,4-Dichloro-6-fluoroaniline (1 equivalent) was reacted with 4-chloro-6-nitroquinazoline (3.5 equivalents), in iso-propylalcohol. After filtration, 4-[(3,4-dichloro-6-fluorophenyl)amino]-6-nitroquinazoline (compound 1) was obtained in 78% yield.

(ii) A solution of 4-[(3,4-dichloro-6-fluorophenyl)amino]-6-nitroquinazoline (1.09 mmol) in 18 ml 9:1 ethanol:water and 11 ml iso-propylalcohol was heated to reflux temperature. 250 μl hydrazine hydrate and 0.5 ml Raney®Nickel (in water) were added thereafter. After 30 minutes, additional 50 μl of hydrazine hydrate was added, and the reflux was maintained for 20 minutes. Filtration, evaporation and silica gel chromatography (using 90% CH$_2$Cl$_2$/10% MeOH as elute) gave 4-[(3,4-dichloro-6-fluorophenyl)amino]-6-aminoquinazoline (compound 2) in 75% yield.

(iii) Acryloyl chloride was reacted with 4-[(3,4-dichloro-6-fluorophenyl)amino]-6-aminoquinazoline in THF, at 0° C. The final product was obtained in quantitative yield.

Synthesis of Carbon-11 Labeled α,β-unsaturated [4-(phenylamino)quinazoline-6-yl]acrylamides—General Procedure:

The radiosynthesis is carried out by a fully automated route using the Nuclear Interface MeI module. carbon-11 CO$_2$ (Approx. 700 mCi) is trapped at −160° C., and transferred thereafter, using a stream of argon, to a first reactor that contains vinyl magnesium bromide in THF (90% trapping efficiency). Addition of phtaloyl dichloride and ditert-butylpyridine gives the carbon-11 labeled acryloyl chloride. The labeled acryloyl chloride is distilled during 4 minutes at 100° C., using a stream of argon (20–30 ml/min) to a second reactor, which contains 300 μl of THF at −50° C. At the end of the distillation the temperature is raised to 10° C., and a solution of 5–7 mg of 4-(phenylamino)-6-aminoquinazoline in 300 μl of anhydrous THF is added thereto. After two minutes, 600 μl of a HPLC solvent (such as 48% CH$_3$CN in 52% acetate buffer pH=3.8) is added and the solution is injected to HPLC (C18-reverse phase-prep Column, 15 ml/min. flow rate). The product is collected into a solid phase extraction vial containing 50 ml of water and 1 ml of 1 M NaOH. The solution is passed through an activated, pre-washed (with 10 ml water) C18 cartridge, and washed with 10 ml sterile water. The product is eluted using 1 ml of ethanol followed by 5 ml of saline and collected in a sterile product vial in 18% decay-corrected (EOB) radiochemical yield. Overall synthesis time, including purification, is 35 minutes.

Synthesis of Carbon-11 Labeled {4-[(3,4-dichloro-6-fluorophenyl)amino]quinazoline-6-yl}acrylamide (Compound 3)

carbon-11 labeled acryloyl chloride was obtained by the general procedure described hereinabove, and was reacted for two minutes with 5–7 mg of 4-[(3,4-dichloro-6-fluorophenyl)amino]-6-aminoquinazoline. HPLC solvent (600 µl of 48% $CH_3CN$ and 52% acetate buffer pH=3.8) was added thereafter, and the solution was injected to HPLC apparatus as described hereinabove. The retention time of the product was 22 minutes. The product was collected, passed through the activated, water-washed, C18 cartridge and collected in a sterile product vial in 18% decay-corrected (EOB) radiochemical yield. The radiochemical purity thereof was analyzed by reverse phase HPLC (µ Bondapak analytical column), using 40% $CH_3CN$ in 60% acetate buffer (pH=3.8) as elute, at a flow rate of 1.7 ml/min (retention time was 11.7 minutes), and found to be 100%, SA of 1700 Ci/mmol.

Synthesis of Fluorine-18 Labeled α,β-unsaturated [4-(phenylamino)quinazolin-6-yl]acrylamides—General Procedure:

The Kryptofix®2.2.2—potassium $^{18}F$-fluoride—DMSO solution described above is added to 2–3 mg of a pre-selected dinitrobenzene in a screw-top test tube (8 ml, Corning). The tube is capped, shaken and heated in a microwave for 3.5 minutes. The tube is cooled in an ambient water bath, and the contents thereof are diluted with 10 ml of water and loaded onto an activated (ethanol) and equilibrated (water) C18 Sep-Pak (classic, short body, Waters). The cartridge is washed with water (10 ml) and the desired corresponding intermediate, fluorine-18 labeled fluoronitrobenzene, is eluted with ethanol (2 ml) into a small glass test tube. The reduction vessel is prepared by adding to a flat-bottomed glass vial (25 ml), sequentially, a few borosilicate glass beads, 100 µl 4:1 ethanol-water, 250 µl Raney®Nickel slurry, and 60 µl hydrazine monohydrate. After capping with a septum-equipped screw cap (vented with a large diameter needle) the vial is shaken and placed in a 40° C. heating block. The ethanolic fluorine-18 labeled fluoronitrobenzene solution is diluted with 0.5 ml water and added slowly to the reduction vessel. After 5 minutes, the vessel is cooled in an ambient water bath, and the vial content is filtered through a 0.45 µm filter (Puradisc, polypropylene, Whatman) into another flat-bottomed 25 ml vial. Eight ml of water and 10 ml of ether are then added to the filtered solution, and by capping and inverting several times to mix, the corresponding fluorine-18 labeled fluoroaniline reduction product is extracted into the ether layer. An 8 ml screw-top test tube is then charged with a solution of 4–5 mg of 4-chloro-6-nitroquinazoline in 300 µl 2-propanol. The ethereal radiolabeled aniline solution is added to the tube by passing it through $MgSO_4$ (2 grams) and a new 0.45 µm filter. The ether is removed under a stream of helium, while warming the tube in an ambient water bath. Concentrated HCl (1 µl) is added thereafter and the capped tube is heated in a 110° C. oil bath for 15 minutes. After cooling the tube in ambient water, the acid is neutralized and the free base is liberated with the addition of 50 µl of 5M NaOH. Dichloromethane (0.3 ml) and hexane (0.3 ml) are added to the tube and the solution is filtered through a 0.2 µm filter (Acrodisc, nylon. Gelman). The fluorine-18 labeled 4-[(fluorophenyl)amino]-6-nitroquinazoline is purified by silica SEP-PAK and reduced to obtain the amine derivative thereof, which is further reacted with acryloyl chloride as described herein.

Synthesis of Fluorine-18 Labeled {4-[(3,4-dichloro-6-fluorophenyl)amino]quinazoline-6-yl}acrylamide (Compound 3)

Fluorine-18 labeled 4-[(3,4-dichloro-6-fluorophenyl)amino]-6-nitro quinazoline (compound 1) was obtained by the radiosynthesis procedure described hereinabove, using 2–3 mg of 1,2-dichloro-4,5-dinitrobenzene in the reaction with the $^{18}F$-fluoride ion to provide 1,2-dichloro-4-$^{18}F$-fluoro-5-nitrobenzene, which was reduced to the corresponding aniline and reacted with 4-chloro-6-nitroquinazoline as described. The fluorine-18 labeled 4-[(3,4-dichloro-6-fluorophenyl)amino]-6-nitroquinazoline was further reacted as described to yield the final fluorine-18 labeled product.

Synthesis of Bromine-76 Labeled and Bromine-77 Labeled {4-[(3-bromophenyl)amino]quinazolin-6-yl}acrylamide:

3-Bromoaniline is coupled with 4-chloro-6-nitroquinazoline, to produce 4-[(3-bromophenyl)amino]-6-nitroquinazoline, which is reduced thereafter to the corresponding 6-aminoquinazoline. The 4-[(3-bromophenyl)amino]-6-aminoquinazoline is then reacted with bistributyltin, using tetrakis(triphenylphosphine)palladium in triethylamine solution as the reaction catalyst. The stanylated quinazoline is then reacted with bromine-76 or bromine-77, in the presence of an oxidizing agent, to produce bromine-76 labeled or bromine-77 labeled 4-[(3-bromophenyl)amino]-6-aminoquinazoline, which is further reacted with acryloyl chloride as described, to yield the final bromine-76 labeled or bromine-77 labeled product.

Synthesis of Iodine-123 Labeled and Iodine-124 Labeled {4-[(3-iodophenyl)amino]quinazolin-6-yl}acrylamide:

3-Bromoaniline is coupled with 4-chloro-6-nitroquinazoline, to produce 4-[(3-bromophenyl)amino]-6-nitroquinazoline, which is reduced thereafter to the corresponding 6-aminoquinazoline. The 4-[(3-bromophenyl)amino]-6-aminoquinazoline is then reacted with bistributyltin, using tetrakis(triphenylphosphine)palladium in triethylamine solution as the reaction catalyst. The stanylated quinazoline is then reacted with iodine-123 or iodine-124, in the presence of an oxidizing agent, to produce iodine-123 labeled or iodine-124 labeled 4-[(3-bromophenyl)amino]-6-aminoquinazoline, which is further reacted with acryloyl chloride as described, to yield the final iodine-123 labeled or iodine-124 labeled product.

Activity Assays:

Autophosphorylation Inhibition Experiments in A431 Cell Lysate:

EGFR-TK source: As a source of EGFR-TK, A431 human epidermoid carcinoma cell lysate was used. A431 cells were grown in DMEM containing 10% fetal calf serum and antibiotics (penicillin and streptomycin). After several days, the cells were removed from the flasks by incubation at 37° C. with PBS/1 mM EDTA buffer for 1 hour. The pellet obtained with centrifugation of the cell suspension (600 g×5 minutes at room temperature) was then resuspended in lysis buffer (0.02 M Hepes pH 7.4, 0.125 M NaCl, 1% Triton X-100, 10% glycerol) and left in ice for 10 minutes. Cell lysate was obtained with a further centrifugation (10,000 rpm×10 minutes at 4° C.), and the supernatant was collected and frozen at −70° C. in aliquots.

ELISA assay: EGFR-TK autophosphorylation $IC_{50}$ values were obtained by means of an ELISA assay. All the following incubations were performed at room temperature and with constant shaking. After each step the plate was washed with water (×5) and TBST buffer (×1). The final volume for each well was 150 μl.

A Corning 96 well ELISA plate was coated with monoclonal anti EGFR antibody m108 (Sugen Inc.) diluted in PBS (pH 8.2), and kept overnight at 4° C. After removing the unbound m108, the plate was washed and PBS containing 5% milk (1% fat) was added for the blocking (25 minutes).

One aliquot of A431 cell lysate was thawed and added to the plate. The amount of lysate was defined according to a previous test performed without inhibitors for the definition of the best ratio between the amount of m108 and the amount of EGFR-TK in A431 cell lysate.

After 25 minutes, seven different concentrations of each inhibitor were added, and for each case one well was left as a zero-inhibition control (no inhibitor) and one well was left as a zero-EGFR-TK control (no lysate). The inhibitors were diluted in TBS/DMSO and the final concentration of DMSO was 0.05% in each well (including the controls).

After 25 minutes, and without washing the plate, ATP/MnCl$_2$ solution was added in each well. The final concentration was 3 μM ATP/5 mM MnCl$_2$. In this step the temperature was kept at 26° C. and the plate was under constant shaking. The incubation with ATP/MnCl$_2$ was for 5 minutes.

Then, to stop the phosphorylation reaction, EDTA was added (pH 8, final concentration in each well 20 mM) and after 1 minute all the plate was washed.

Afterward, polyclonal anti-phosphotyrosine serum (Sugen, Inc.) was added (dilution of antibody in TBST containing 5% milk). The incubation was for 45 minutes.

For the calorimetric detection of phosphotyrosine in EGFR-TK, TAGO anti-rabbit peroxidase conjugate antibody (Sugen, Inc.) was added in TBST/5% milk solution (45 minutes).

After washing, the calorimetric reaction was performed by adding ABTS/H$_2$O$_2$ in citrate-phosphate buffer. After 5–10 minutes the plate was read on Dynaytec MR 5000 ELISA reader at 405 nm.

The analysis of the data was performed using GraphPad Prism, version 2.01 (Graph[ad Software, Inc.).

Autophosphorylation Inhibition Experiments in Intact A431 Cells:

A431 cells (10$^6$) were seeded in 6-well plates and grown to 60–80% confluence in DMEM (high glucose) containing 10% fetal calf serum (FCS) and antibiotics at 37° C. The cells were then exposed to serum-free medium, at 37° C., for 18 hours.

Irreversibility assay: Variable concentrations of the inhibitor, ranging from 0.05 nM to 50 nM, were added to A431 cells for 2 hours incubation. The inhibitor was diluted in vehicle/DMSO and the final concentration of DMSO was 0.05% in each well). The medium was replaced thereafter with an inhibitor/FCS-free medium and the cells were left for either 2 or 8 hours, at 37° C. During the 8 hours period, the medium was changed three more times. After the post-incubation period, the cells were stimulated with EGF (20 ng/ml) for 5 minutes and then washed with PBS. Whole-cell lysates were obtained by scraping the cells into the well with 0.4 ml of Leammli buffer (10% glycerol, 3% sodium dodecyl sulfate, 5% b-mercaptoethanol, 50 mM Tris pH 6.8) that contained 0.001% bromophenol blue, and boiling for 5 minutes. The samples were kept at −20° C., prior to the protein determination assay described herein below.

EGFR autophosphorylation inhibition rate measurements: A431 cells (6×10$^5$) were incubated with the inhibitor at room temperature for different times, ranging from 1 minute to 10 minutes. After the incubation, the medium was replaced with an inhibitor/FCS-free medium, the cells were kept at 37° C. for either 1 or 8 hours, stimulated thereafter with EGF and lysated as described hereinabove. The protein determination assay was then performed once with n=1 for each time point of the 1 hour post-incubation set of cells left, and with n=2 (for each time point) for the 8 hours post-incubation set of cells.

Protein determination assay: The amount of protein in each lysate was determined by a filter paper assay: Aliquots (3 ml) from each extract were loaded onto a strip (1×3 cm) of Whatman blotting paper and immersed into filtered dyeing solution (0.25% comassie blue, 40% MeOH, 10% acetic acid) for 20 minutes at room temperature with gentle shaking. The strips were then washed (3×15 minutes) with fading solution (20% MeOH, 7% acetic acid) and dried. Each strip was extracted by constant shaking in sodium dodecyl sulfate solution (3%, 500 ml, 37° C.). After 1 hour the eluted samples were transferred to 96-well plates and read at 595 nm in a microplate reader (ELX 800, Biotek Instruments, Inc.). A standard curve was prepared using BSA (1 mg/ml).

Western blots: Identical protein amounts from each lysate sample were loaded onto polyacrylamide gel (6% or 10%), separated by electrophoresis (Hoefer Pharmacia Biotech Inc., San Francisco, USA) and transferred to nitrocellulose membrane (power supply: EPS 500/400, Amersham Pharmacia Biotech; nitrocellulose extra blotting membranes: Sartorius AG, Goettingen, Germany). A standard high molecular weight solution was loaded as a reference. For visualization of molecular weight bands, the membrane was immersed in Ponceau reagent (0.05% Ponceau, 5% acetic acid) for a few minutes, and then washed twice with TTN (10 mM Tris pH 7.4, 0.2% TWEEN 20, 170 mM NaCl) and once with water. The membrane was blocked overnight in TTN containing 5% milk (1% fat) (blocking TTN) and incubated for 90 minutes with PY20 antiphosphotyrosine antibody (Santa Cruz Biotechnology Inc., Santa Cruz, USA) diluted 1:2,000 in blocking TTN. The membrane was then washed with TTN (3×5 minutes), incubated for 90 minutes with a horseradish peroxidase-conjugated secondary antibody (Goat anti-mouse IgG H+L, Jackson ImResearch Laboratories, Inc., diluted 1:10,000 in blocking TTN), and finally washed again with TTN (3×5 minutes). The membrane was incubated in a luminol-based solution (1 minute, 0.1 M Tris pH 8.5, 250 μM luminol, 400 μM p-cumaric acid, 0.033% H$_2$O$_2$) and visualized using chemiluminescent detection.

Quantification of the EGFR-P (protein) bands density obtained was performed using Adobe Photoshop 5.0ME and NIH image 1.16/ppc programs.

Experimental Results

In a quest for radiolabeled irreversible EGFR-TK inhibitors for use in radioimaging and radiotherapy, a derivative of [4-(phenylamino)quinazoline-6-yl]acrylamide (Compound 3) was prepared as an exemplary compound for other radiolabeled [4-(phenylamino)quinazolines substituted by α,β-unsaturated carboxylic derivatives. This class of compounds is prepared by reacting an aniline derivative with 4-chloroquinazoline substituted by a reactive group, and reacting the reactive obtained product with a reactive α,β-unsaturated carboxylic derivative to produce the final compound.

{4-[(3,4-dichloro-6-fluorophenyl)amino]quinazoline-6-yl}acrylamide (Compound 3) was prepared by reacting the corresponding aniline derivative with 4-chloro-6- nitroquinazoline to produce compound 1 (Scheme 4), reducing the nitro group of compound 1 to the amino group, reducing the nitro group to an amino group using an ethanolic solution of hydrazine hydrate and Raney®Nickel as described, to produce compound 2 and reacting compound 2 with acryloyl chloride, at 0° C., to produce the final product Compound 3 (Scheme 4).

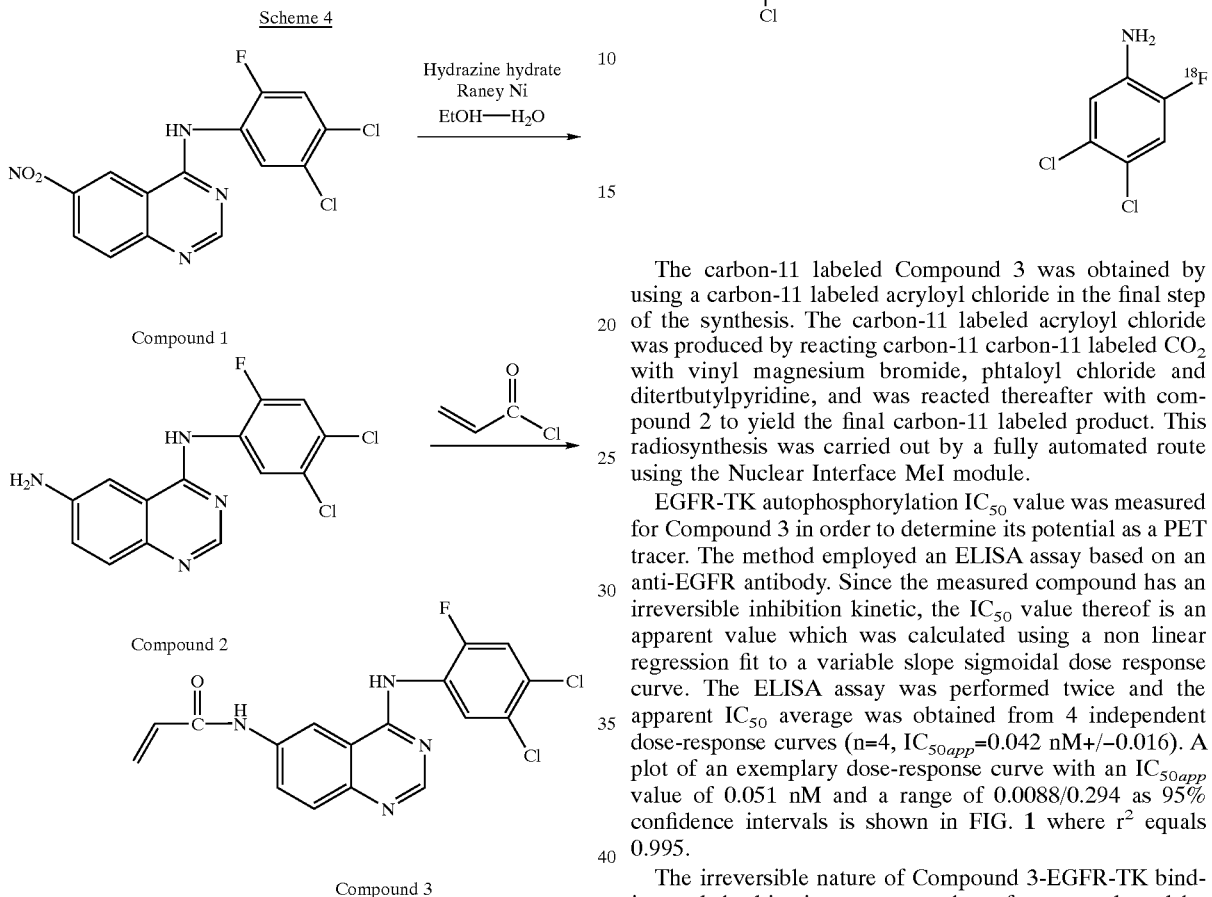

A radiolabeled Compound 3 was obtained by two optional labeling strategies. The first strategy involves the use of fluorine-18 in order to label the aniline moiety at position 6 thereof, using known procedures [17], while the second involves the use of carbon-11 labeled acryloyl synthon [18] at the final synthesis step.

Thus, fluorine-18 labeled Compound 3 was obtained by reacting 1,2-dichloro-4,5-nitrobenzene with potassium fluoride and Kryptofix®2.2.2 as phase transfer catalyst in DMSO solution. The fluorine-18 labeled product was then reduced in ethanolic solution of hydrazine hydrate and Raney®Nickel to produce the fluorine-18 labeled 3,4-dichloro-6-fluoroaniline (labeled compound 1, Scheme 5). The final fluorine-18 labeled product was obtained by using the steps described hereinabove (Scheme 4).

Scheme 5

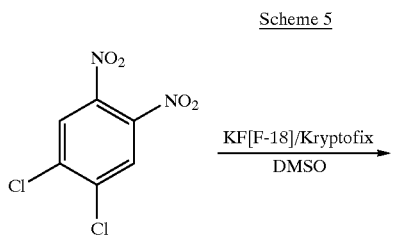

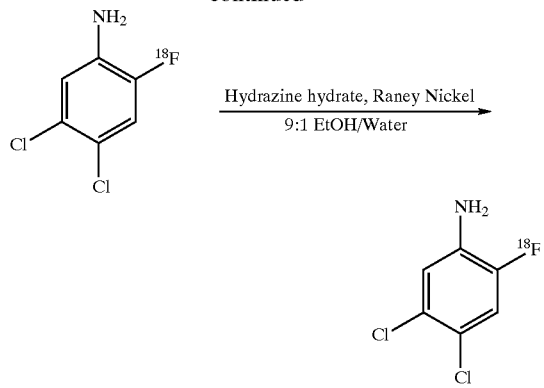

The carbon-11 labeled Compound 3 was obtained by using a carbon-11 labeled acryloyl chloride in the final step of the synthesis. The carbon-11 labeled acryloyl chloride was produced by reacting carbon-11 carbon-11 labeled $CO_2$ with vinyl magnesium bromide, phtaloyl chloride and ditertbutylpyridine, and was reacted thereafter with compound 2 to yield the final carbon-11 labeled product. This radiosynthesis was carried out by a fully automated route using the Nuclear Interface MeI module.

EGFR-TK autophosphorylation $IC_{50}$ value was measured for Compound 3 in order to determine its potential as a PET tracer. The method employed an ELISA assay based on an anti-EGFR antibody. Since the measured compound has an irreversible inhibition kinetic, the $IC_{50}$ value thereof is an apparent value which was calculated using a non linear regression fit to a variable slope sigmoidal dose response curve. The ELISA assay was performed twice and the apparent $IC_{50}$ average was obtained from 4 independent dose-response curves (n=4, $IC_{50app}$=0.042 nM+/−0.016). A plot of an exemplary dose-response curve with an $IC_{50app}$ value of 0.051 nM and a range of 0.0088/0.294 as 95% confidence intervals is shown in FIG. 1 where $r^2$ equals 0.995.

The irreversible nature of Compound 3-EGFR-TK binding and the kinetic parameters thereof were evaluated by measuring the inhibition of EGFR-TK autophosphorylation in intact A431 cell line.

Figure 2:
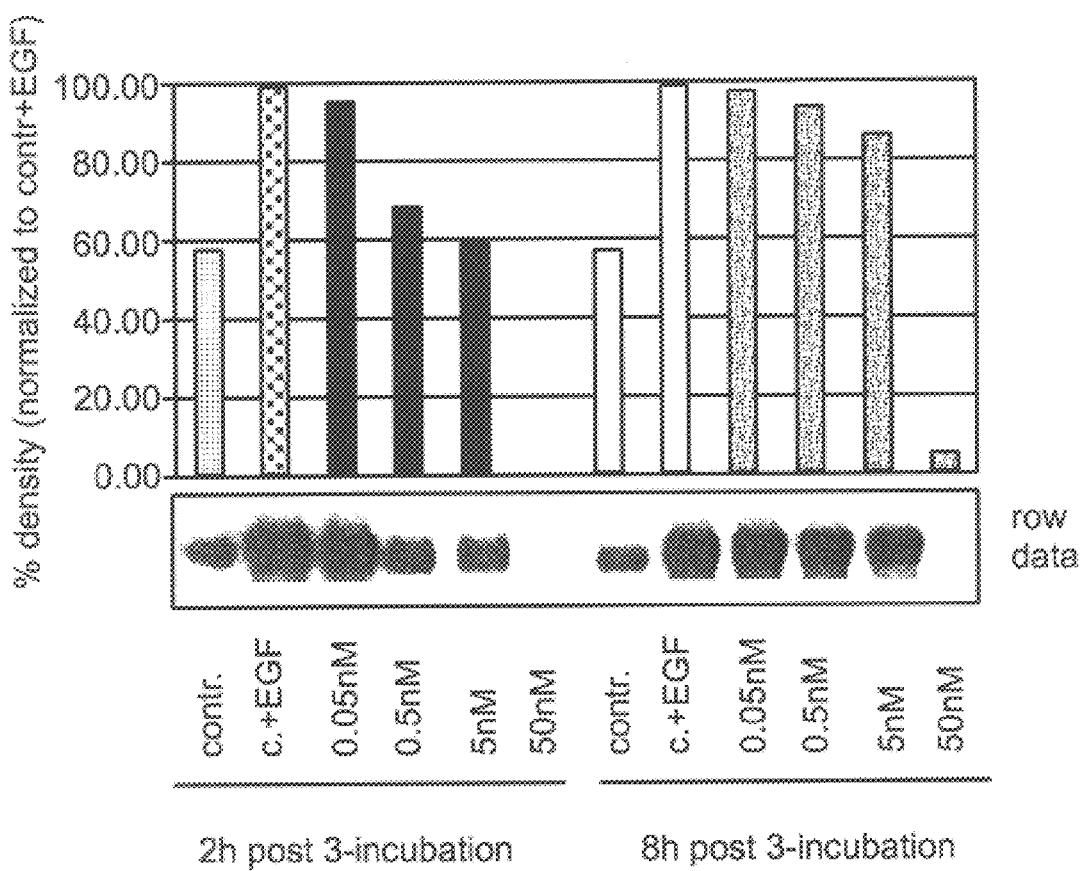
FIG. 2 is a bar graph presenting the EGFR autophosphorylation level in A431 cells following incubation with various concentrations of Compound 3 and EGF stimulation-lysis at 2 hours and 8 hours post-incubation time (white bars with and without dots are control without EGF stimulation, bars with squared pattern are controls stimulated with EGF and the other bars show the described EGFR autophosphorylation level). The inset below shows a Western blot for each concentration at 2 hours and 8 hours post-incubation time and is coaligned with the bars.

In order to demonstrate the irreversibility of the binding of Compound 3 to the receptor, the cells were incubated with variable inhibitor concentrations for two hours. After the incubation, the media was replaced with inhibitor/FCS-free media and the inhibition effect was measured and compared after 2 and 8 hours. As is presented in FIG. 2, after 2 hours in an inhibitor/FCS-free media about 35%, 40% and about 100% inhibition was obtained at 0.5 nM, 5 nM and 50 nM inhibitor concentrations, respectively. Furthermore, it is shown that even after 8 hours post-incubation the inhibition was still evident for a 50 nM inhibitor concentration (about 97%). This high autophosphorylation inhibition obtained at this concentration after both 2 hours and 8 hours post-incubation periods is attributed to the high ratio of pmoles inhibitor/pmoles EGFR at this concentration. However, a small quantity of phosphorylation is observed at 50 nM after 8 hours, which can be explained by a proliferation of cells and a new biosynthesis/expression on the cell surface of new receptors.

Figure 3:
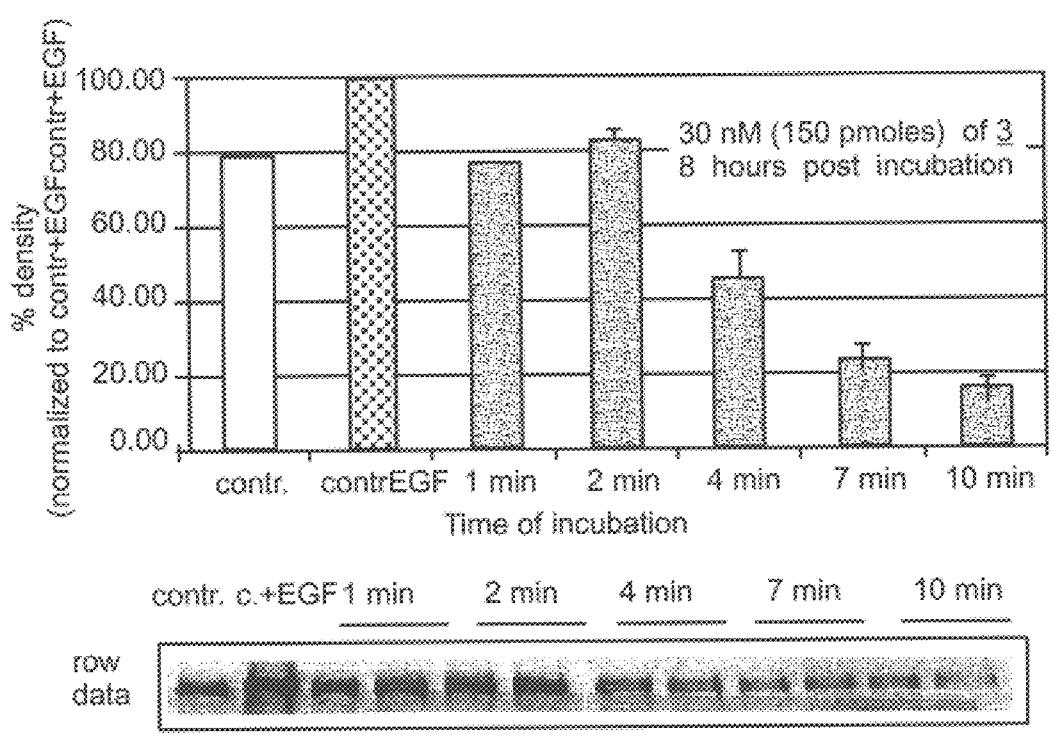
FIG. 3 is a bar graph presenting the autophosphorylation levels of EGFR in A431 cells after varying incubation time with Compound 3, at 8-hour post-incubation time (the bars are the result of two determinations). The inset below shows a Western blot for each data point and is coaligned with the bars.
Figure 4:
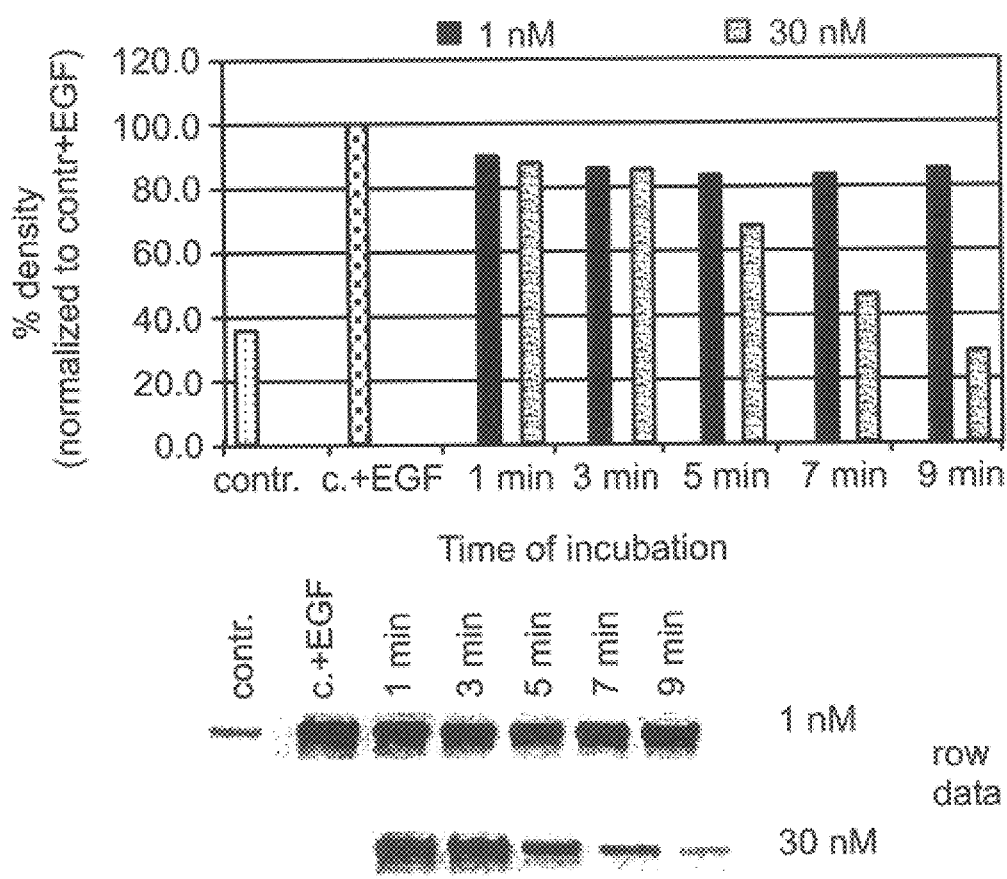
FIG. 4 is a bar graph presenting the autophosphorylation levels of EGFR in A431 cells after varying incubation time with 1 nM and 30 nM of Compound 3, at 1-hour post-incubation time. The inset below shows a Western blot for each data point and is coaligned with the bars.

FIGS. 3 and 4 present the decrease of EGFR autophosphorylation following varying incubation times of intact A431 cells with Compound 3 and varying inhibitor concentrations, respectively. The EGFR autophosphorylation level was measured at 1 hour and 8 hours post-incubation periods.

As is shown in FIG. 3, 10 minutes incubation time and 30 nM inhibitor concentration were needed to obtain 80% inhibition after 8 hours post-incubation period. The same effect is shown in FIG. 4 for 9 minutes incubation time and 30 nM inhibitor concentration. These results reflect the nature of the irreversible binding of the inhibitor, which maintains about the same inhibition potency at both 1 hour and 8 hours post-incubation periods.

FIG. 4 further supports the observed results by presenting this high inhibition effect only at high inhibitor concentrations.

Thus, a method was developed for the synthesis of radiolabeled irreversible EGFR-TK ATP-site inhibitors. A member of these inhibitors family was found to be highly potent irreversible EGFR-TK inhibitor and was successfully radiolabeled with both carbon-11 and fluorine-18 in yields and reaction times suitable for further use as a biological tracer. Therefore, this class of carbon-11 labeled and fluorine-18 labeled compounds can be used to measure differences in EGFR-TK expression and ATP binding site fractional occupancy in vitro and in vivo and be used as efficient PET tracers in, for example, cancer diagnosis, staging and therapy protocol selection, e.g., in predicting which patients would benefit from EGF-directed therapeutic approaches such as those based on anti-EGF antibodies, EGF-directed fusion toxins, or EGFR-TK inhibitors. Another member of these inhibitors family, which is radiolabeled with either a radioactive bromine or a radioactive iodine can be used for radioimaging and radiotherapy with respect to EGFR-TK expression. Thus, bromine-76 labeled and iodine-124 labeled compounds can be used for PET radioimaging and iodine-123 labeled compounds can be used for SPECT radioimaging, while bromine-77 labeled and iodine-124 labeled compounds can be used for radiotherapy.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

1. Escobar, N. I.; Morales, A. M.; Ducongu, J.; Torres, I. C.; Fernandez, E.; Gomez, J. A. Pharmacokinetics, biodistribution and dosimetry of 99mTc-labeled anti-human epidermal growth factor receptor humanized monoclonal antibody R3 in rats. *Nucl. Med. Biol.* 1998, 25, 17–23.
2. Iznaga-Escobar, N.; Torres, L. A.; Morales, A.; Ramos, M.; Alvarez, I.; Perez, N.; Fraxedas, R.; Rodriguez, O.; Rodriguez, N.; Perez, R.; Lage, A.; Stabin, M. G. *J. Nucl Med.* 1998, 39, 15–23.
3. Capala, J.; Barth, R. F.; Bailey, M. Q.; Fenstermaker, R. A.; Marek, M. J.; Rhodes, B. A. Radiolabeling of epidermal growth factor with Tc and in vivo localization following intracerebral injection into normal and glioma-bearing rats. *Bioconjug. Chem.* 1997, 8, 289–295.
4. Holmberg, A.; Marquez, M.; Westlin, J. -E.; Nilsson, S. Labeling of polypeptides with technetium-99m using a dextran spacer. *Cancer Res.* 1995, 55, 5710s–5713s.
5. Remy, S.; Reilly, R. M.; Sheldon, K.; Gariepy, J. A new radioligand for the epidermal growth factor receptor: In labeled human epidermal growth factor derivatized with a bifunctional metal-chelating peptide. *Bioconjugate Chem.* 1995, 6, 683–690.
6. Reilly, R. M.; Gariepy, J. Investigation of factors influencing the sensitivity of tumor imaging with phantoms and a receptor binding radiopharmaceutical. *J. Nucl. Med.* 1996, 37 (supplement), 199P (abstract number 911).
7. Scott-Robson, S.; Capala, J.; Malmborg, P.; Lundqvist, H. Production of Br and its use in labeling proteins. *Acta Radiol. Suppl.* 1991, 376, 64.
8. Scott-Robson, S.; Capala, J.; Carlsson, J.; Malmborg, P.; Lundqvist, H. Distribution and stability in the rat of a Br/I-labeled polypeptide, epidermal growth factor. *Int. J. Appl. Instrum.* [B] 1991, 18, 241–246.
9. Fry, D. W.; Kraker, A. J.; McMichael, A.; Ambroso, L. A.; Nelson, J. M.; Leopold, W. R.; Connors, R. W.; Bridges, A. J. A specific inhibitor of the epidermal growth factor receptor tyrosine kinase. *Science* 1994, 265, 1093–1095.
10. Levitzki, A.; Gazit, A. *Science* 1995 267, 1782–1788.
11. Mulholland, G. K.; Winkle, W.; Mock, B. H.; Sledge, G. J. *Nucl Med.* 1995, 36 (supplement), 71P.
12. Johnstrom P., Fredriksson A., Thorell J. -O., and Stone-Elander S. *J. Labelled Cpd. Radiopharm.* 41: 623 (1998).
13. Mulholland, G. K.; Zheng, Q. -H.; Winkle, W. L.; Carlson, K. A. *J. Nucl. Med.* 1997, 38, 141P (abstract number 529).
14. Eckelman, W. C. The application of receptor theory to receptor-binding and enzyme-binding oncologic radiopharmaceuticals. *Nucl. Med. Biol.* 1994, 21, 759–769.
15. Smaill J. B.; ReG. W.; Loo J. A.; Greis K. D.; Chan O. H.; Reyner E. L.; Lipka E.; Showalter H. D.; Vincent P. W.; Elliott W. L.; Denny W. A. *J Med Chem.* 43, 1380–1397 (2000).
16. Smaill J. B. et al. *J Med Chem,* 42, 1803–1815 (1999).
17. Mishani E., Cristel M. E., Dence C. S., McCarthy T. J., and Welch M. J.- *Nucl. Med. Biol.* 24: 269 (1997).
18. Lasne M. C.; Cairon P.; Barre L. *Appl. Radiat. Isot.,* 43, 621–625, (1992).

What is claimed is:

1. A radiolabeled compound of a formula:

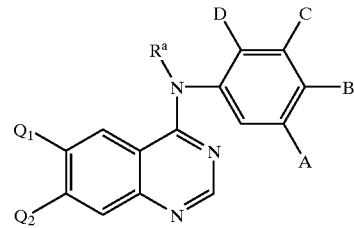

Formula I wherein:

Q1 is X—Y(=O)—Z and Q2 is selected from the group consisting of hydrogen, halogen, alkoxy, hydroxy, thiohydroxy, thioalkoxy, alkylamino and amino, or Q1 is selected from the group consisting of hydrogen, halogen, alkoxy, hydroxy, thiohydroxy, thioalkoxy, alkylamino and amino and Q2 is X—Y(=O)—Z;

X is selected from the group consisting of —NR$^1$—, —O—, —NH—NR$^1$—, —O—NR$^1$—, NH—CHR$^1$—, —CHR¹—NH—, —CHR¹—O—, —O—CHR¹—, —CHR¹—CH₂— and —CHR¹—S— or absent;

Y is selected from the group consisting of a non-radioactive carbon and a radioactive carbon;

Z is selected from the group consisting of —R²C=CHR³, —C≡C—R³ and —R²C=C=CHR³;

$R^a$ is selected from the group consisting of hydrogen or alkyl having 1–8 carbon atoms;

A, B, C and D are each independently selected from the group consisting of hydrogen, a non-radioactive derivatizing group and a radioactive derivatizing group selected from a radioactive bromine, a radioactive iodine and a radioactive fluorine;

R¹ is selected from the group consisting of hydrogen, and substituted or non-substituted alkyl having 1–6 carbon atoms;

R² is selected from the group consisting of hydrogen, halogen and alkyl having 1–6 carbon atoms; and R³ is selected from the group consisting of hydrogen, halogen, carboxy, alkenyl, alkoxy carbonyl, substituted or non-substituted alkyl having 1–6 carbon atoms and substituted or non-substituted phenyl;

provided that the compound comprises at least one radioactive atom.

2. The radiolabeled compound of claim 1, wherein said non-radioactive derivatizing group is selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano.

3. The radiolabeled compound of claim 1, wherein Q1 is X—Y(=O)—Z and Q2 is selected from the group consisting of hydrogen, halogen, alkoxy, hydroxy, thiohydroxy, thioalkoxy, alkylamino and amino.

4. The radiolabeled compound of claim 1, wherein Q1 is X—Y(=O)—Z and Q2 is hydrogen.

5. The radiolabeled compound of claim 4, wherein X is said —NR¹— and Z is said —R²C=CHR³.

6. The radiolabeled compound of claim 5, wherein each of R¹, R² and R³ is hydrogen.

7. The radiolabeled compound of claim 1, wherein Y is said radioactive carbon.

8. The radiolabeled compound of claim 1, wherein at least one of A, B, C and D is said radioactive fluorine.

9. The radiolabeled compound of claim 1, wherein D is said radioactive fluorine.

10. The radiolabeled compound of claim 9, wherein A and B are each chlorine and C is hydrogen.

11. The radiolabeled compound of claim 1, wherein A is said radioactive bromine.

12. The radiolabeled compound of claim 1, wherein A is said radioactive iodine.

13. The radiolabeled compound of claim 1, wherein said radioactive carbon is carbon-11.

14. The radiolabeled compound of claim 13, wherein A and B are each chlorine, C is hydrogen and D is fluorine.

15. The radiolabeled compound of claim 1, wherein said radioactive fluorine is fluorine-18.

16. The radiolabeled compound of claim 1, wherein said radioactive bromine is bromine-76 or bromine-77.

17. The radiolabeled compound of claim 1, wherein said radioactive iodine is iodine-123 or iodine-124.

18. A pharmaceutical composition comprising as an active ingredient the radiolabeled compound of claim 1 and a pharmaceutical acceptable carrier.

19. A method of monitoring the level of epidermal growth factor receptor within a body of a patient comprising:

(a) administering to the patient the radiolabeled compound of claim 1; and (b) employing a nuclear imaging technique for monitoring a distribution of the compound within the body or within a portion thereof.

20. The method of claim 19, wherein said technique is positron emission tomography.

21. The method of claim 19, wherein said technique is single photon emission computed tomography.

22. A method of radiotherapy comprising administering to a patient a therapeutically effective amount of the radiolabeled compound of claim 1.

23. A method of synthesizing a radiolabeled compound of a formula:

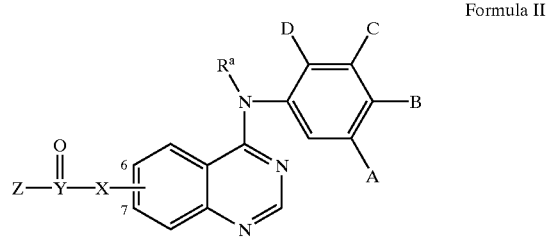

Formula II wherein:

X—Y(=O)—Z is at position 6 or 7 of the quinazoline ring;

X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;

Y is carbon-11;

Z is selected from the group consisting of —R²C=CHR³, —C≡C—R³ and —R²C=C=CHR³;

$R^a$ is selected from the group consisting of hydrogen or alkyl having 1–8 carbon atoms;

A, B, C and D are each independently selected from the group consisting of hydrogen and a non-radioactive derivatizing group;

R¹ is selected from the group consisting of hydrogen, and substituted or non-substituted alkyl having 1–6 carbon atoms;

R² is selected from the group consisting of hydrogen, halogen and alkyl having 1–6 carbon atoms; and R³ is selected from the group consisting of hydrogen, halogen, carboxy, alkenyl, alkoxy carbonyl, substituted or non-substituted alkyl having 1–6 carbon atoms and substituted or non-substituted phenyl, the method comprising:

(a) coupling an aniline derivatized by said $R^a$, A, B, C and D with a 4-chloroquinazoline substituted at position 6 or 7 by a reactive group, so as to produce a reactive 4-(phenylamino)quinazoline derivatized by said A, B, C and D; and (b) reacting said reactive 4-(phenylamino)quinazoline with a reactive carbon-11 labeled α,β-unsaturated carboxylic derivative.

24. The method of claim 23, wherein said non-radioactive derivatizing group is selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano.

25. The method of claim 23, wherein said X—Y(=O)—Z is at position 6 of the quinazoline ring.

26. The method of claim 23, wherein said reactive 4-(phenylamino)quinazoline is 4-(phenylamino)-6-nitroquinazoline, the method further comprising, prior to step (b):
 (c) reducing said 4-(phenylamino)-6-nitroquinazoline so as to produce a 4-(phenylamino)-6-aminoquinazoline derivatized by said A, B, C and D.

27. The method of claim 23, wherein said reactive carbon-11 labeled α,β-unsaturated carboxylic derivative is carbon-11 labeled acryloyl chloride.

28. A method of synthesizing a radiolabeled compound of a formula:

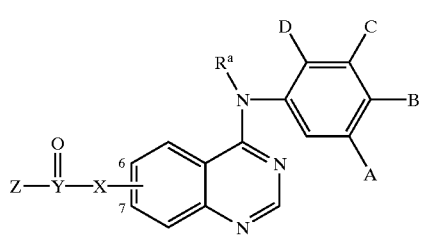

Formula II wherein:
 X—Y(=O)—Z is at position 6 or 7 of the quinazoline ring;
 X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;
 Y is a non-radioactive carbon;
 Z is selected from the group consisting of —R²C=CHR³, —C≡C—R³ and —R²C=C=CHR³;
 Rᵃ is selected from the group consisting of hydrogen or alkyl having 1–8 carbon atoms;
 A, B, C and D are each independently selected from the group consisting of hydrogen, a non-radioactive derivatizing group and a fluorine-18, provided that at least one of A, B, C and D is said fluorine-18;
 R¹ is selected from the group consisting of hydrogen, and substituted or non-substituted alkyl having 1–6 carbon atoms;
 R² is selected from the group consisting of hydrogen, halogen and alkyl having 1–6 carbon atoms; and
 R³ is selected from the group consisting of hydrogen, halogen, carboxy, alkenyl, alkoxy carbonyl, substituted or non-substituted alkyl having 1–6 carbon atoms and substituted or non-substituted phenyl, the method comprising:
 (a) preparing a fluorine-18 labeled aniline derivatized by said Rᵃ, A, B, C and D, wherein at least one of A, B, C and D is said fluorine-18;
 (b) coupling said fluorine-18 labeled aniline derivatized by said Rᵃ, A, B, C and D with 4-chloroquinazoline substituted at position 6 or 7 by a reactive group, so as to produce a reactive fluorine-18 labeled 4-(phenylamino)quinazoline derivatized by said A, B, C and D; and
 (c) reacting said reactive fluorine-18 labeled 4-(phenylamino)quinazoline with a reactive α,β-unsaturated carboxylic derivative.

29. The method of claim 28, wherein said non-radioactive derivatizing group is selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano.

30. The method of claim 28, wherein said X—Y(=O)—Z is at position 6 of the quinazoline ring.

31. The method of claim 28, wherein said reactive fluorine-18 labeled 4-(phenylamino)quinazoline is fluorine-18 labeled 4-(phenylamino)-6-nitroquinazoline, the method further comprising, prior to step (c):
 (d) reducing said fluorine-18 labeled 4-(phenylamino)-6-nitroquinazoline, so as to produce a fluorine-18 labeled 4-(phenylamino)-6-aminoquinazoline derivatized by said A, B, C and D.

32. The method of claim 28, wherein said reactive α,β-unsaturated carboxylic derivative is acryloyl chloride.

33. A method of synthesizing a radiolabeled compound of a formula:

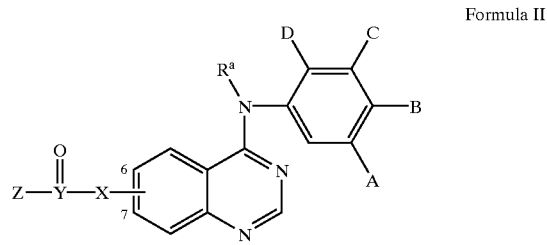

Formula II wherein:
 X—Y(=O)—Z is at position 6 or 7 of the quinazoline ring;
 X is selected from the group consisting of —NR¹—, —O—, —NH—NR¹—, —O—NR¹—, NH—CHR¹—, —CHR¹—NH—, —CHR¹—O—, —O—CHR¹—, —CHR¹—CH₂— and —CHR¹—S— or absent;
 Y is a non-radioactive carbon;
 Z is selected from the group consisting of —R²C=CHR³, —C≡C—R³ and —R²C=C=CHR³;
 Rᵃ is selected from the group consisting of hydrogen or alkyl having 1–8 carbon atoms;
 A, B, C and D are each independently selected from the group consisting of hydrogen, a non-radioactive derivatizing group and a radioactive atom selected from a radioactive bromine and a radioactive iodine, provided that at least one of A, B, C and D is said radioactive bromine or said radioactive iodine;
 R¹ is selected from the group consisting of hydrogen, and substituted or non-substituted alkyl having 1–6 carbon atoms;
 R² is selected from the group consisting of hydrogen, halogen and alkyl having 1–6 carbon atoms; and
 R³ is selected from the group consisting of hydrogen, halogen, carboxy, alkenyl, alkoxy carbonyl, substituted or non-substituted alkyl having 1–6 carbon atoms and substituted or non-substituted phenyl, the method comprising:
 (a) coupling an aniline derivatized by said Rᵃ, A, B, C and D, wherein at least one of A, B, C and D is a halogen, with a 4-chloroquinazoline substituted at position 6 or 7 by a reactive group, so as to produce a reactive 4-(phenylamino)quinazoline derivatized by said A, B, C and D, wherein at least one of A, B, C and D is said halogen;
 (b) radiolabeling said reactive 4-(phenylamino)quinazoline derivatized by said A, B, C and D with a radioactive bromine or a radioactive iodine, so as to produce a radioactive bromine labeled or a radioactive iodine labeled reactive 4-(phenylamino)quinazoline derivatized by said A, B, C and D, wherein at least one of said A, B, C and D is said radioactive bromine or said radioactive iodine; and (c) reacting said radioactive bromine labeled or radioactive iodine labeled reactive 4-(phenylamino)quinazoline with a reactive α,β-unsaturated derivative.

34. The method of claim 33, wherein said radioactive bromine is bromine-76 or bromine-77.

35. The method of claim 33, wherein said radioactive iodine is iodine-123 or iodine-124.

36. The method of claim 33, wherein said non-radioactive derivatizing group is selected from the group consisting of hydrogen, halogen, alkyl, haloalkyl, hydroxy, alkoxy, carboxy, carbalkoxy, thiocarboxy, thiohydroxy, thioalkoxy, alkylsulfinyl, alkylsulfonyl, amino, diamino, carbamyl, dicarbamoyl, nitro and cyano.

37. The method of claim 33, wherein said X—Y(=O)—Z is at position 6 of the quinazoline ring.

38. The method of claim 33, wherein said reactive 4-(phenylamino)quinazoline is 4-(phenylamino)-6-nitroquinazoline, the method further comprising, prior to step (b):

(d) reducing said 4-(phenylamino)-6-nitroquinazoline, so as to produce a 4-(phenylamino)-6-aminoquinazoline derivatized by said A, B, C and D, wherein at least one of said A, B, C and D is said halogen.

39. The method of claim 33, wherein said halogen is bromine.

40. The method of claim 33, wherein said reactive α,β-unsaturated carboxylic derivative is acryloyl chloride.

* * * * *